United States Patent
He et al.

(10) Patent No.: US 11,420,959 B2
(45) Date of Patent: Aug. 23, 2022

(54) DACOS TYPE NNRTIS AMINO ACID ESTER DERIVATIVE, PREPARATION METHOD THEREOF, PHARMACEUTICAL COMPOSITION, AND APPLICATION THEREOF

(71) Applicants: YUNNAN UNIVERSITY, Kunming (CN); KUNMING INSTITUTE OF ZOOLOGY, CHINESE ACADEMY OF SCIENCES, Kunming (CN)

(72) Inventors: Yanping He, Kunming (CN); Hongbin Zhang, Kunming (CN); Yongtang Zheng, Kunming (CN); Yufang Zhang, Kunming (CN); Chengrun Tang, Kunming (CN); Wei Ding, Kunming (CN); Liumeng Yang, Kunming (CN); Yiming Li, Kunming (CN)

(73) Assignees: Yunnan University, Kunming (CN); Kunming Institute of Zoology, Chinese Academy of Sciences, Kunming (CN)

( * ) Notice: Subject to any disclaimer, the term of this patent is extended or adjusted under 35 U.S.C. 154(b) by 89 days.

(21) Appl. No.: 16/977,867

(22) PCT Filed: Mar. 4, 2019

(86) PCT No.: PCT/CN2019/076842
§ 371 (c)(1),
(2) Date: Sep. 3, 2020

(87) PCT Pub. No.: WO2019/170051
PCT Pub. Date: Sep. 12, 2019

(65) Prior Publication Data
US 2021/0040069 A1 Feb. 11, 2021

(30) Foreign Application Priority Data
Mar. 6, 2018 (CN) .................... 201810183281.7

(51) Int. Cl.
*C07D 239/56* (2006.01)
*C07D 403/12* (2006.01)
*A61P 31/18* (2006.01)

(52) U.S. Cl.
CPC ........... *C07D 403/12* (2013.01); *A61P 31/18* (2018.01); *C07D 239/56* (2013.01)

(58) Field of Classification Search
CPC ..................... C07D 239/56; C07D 403/22
See application file for complete search history.

(56) References Cited

FOREIGN PATENT DOCUMENTS

| CN | 102558072 A | 7/2012 |
| CN | 106866548 A | 6/2017 |
| CN | 110483417 A | 11/2019 |

OTHER PUBLICATIONS

International Search Report issued in International Patent Application No. PCT/CN2019/076842, dated May 23, 2019.
Written Opinion of the International Searching Authority issued in International Patent Application No. PCT/CN2019/076842, dated May 23, 2019.
Yan-Ping He et al., "Synthesis and biological evaluation of novel dihydro-aryl/alkylsulfanyl-cyclohexylmethyl-oxopyrimidines (S-DACOs) as high active anti-HIV agents," Bioorg. & Med. Chem., Jan. 2011, pp. 694-697, vol. 21.
Zhi-Kun Rao et al., "Synthesis and anti-HIV-1 activity of S-dihydro(alkyloxy)benzyloxypyrimidine derivatives," Monatsh Chem., Jun. 2008, pp. 967-974, vol. 139.
Stephen M. Berge et al. "Pharmaceutical Salts", Journal of Pharmaceutical Science, Jan. 1977, pp. 1-19, vol. 66, No. 1.
Remington: The Science and Practice of Pharmacy, 21st Ed., Lippincott, Williams & Wilkins (2005).
Hubert Maehr, "A Proposed New Convention for Graphic Presentation of Molecular Geometry and Topography," J Chem. Ed. Feb. 1985, pp. 114-120, vol. 62.
Chinese Office Action issued in Chinese Patent Application No. 2018101832817, dated Dec. 16, 2021.

*Primary Examiner* — Brian E McDowell
(74) *Attorney, Agent, or Firm* — Pilloff Passino & Cosenza LLP; Sean A. Passino; Rachel K. Pilloff

(57) ABSTRACT

Disclosed is a DACOs-type NNRTIs amino acid ester derivative, a preparation method thereof, a pharmaceutical composition, and an application thereof. The structure of the DACOs-type NNRTIs amino acid ester derivative is represented by formula (I). The DACOs-type NNRTIs amino acid ester derivative represented by formula (I) can be used as HIV-1 inhibitors and for the preparation of a drug for treating and/or preventing immunodeficiency viruses.

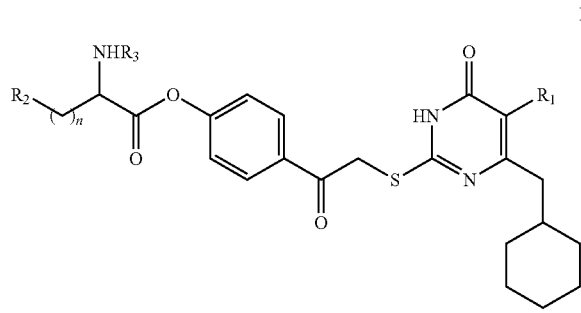

19 Claims, No Drawings

DACOS TYPE NNRTIS AMINO ACID ESTER DERIVATIVE, PREPARATION METHOD THEREOF, PHARMACEUTICAL COMPOSITION, AND APPLICATION THEREOF

The present application claims the benefit of Chinese Patent Application No. CN201810183281.7 filed on Mar. 6, 2018, the contents of which are incorporated herein by reference in its entirety.

TECHNICAL FIELD

The present disclosure pertains to the field of chemical synthesis and pharmaceutical technology, specifically relates to a DACOs-type NNRTIs amino acid ester derivative, and a preparation method, pharmaceutical composition and use thereof.

BACKGROUND ART

Since the discovery of human immunodeficiency virus (HIV) in 1981, the virus has spread at an alarming rate worldwide, and AIDS has become a major infectious disease, which is threatening the health of human being. The treatment of AIDS so far has always been a major technical challenge in the field of clinical medicine. Since the research of AIDS vaccine has not been successful, antiviral therapy is still dominant in the control of AIDS. Nowadays, the drugs approved for the treatment of HIV infection in the United States mostly are based on proteins of the virus itself as the target, including gp41 fusion inhibitors, reverse transcriptase inhibitors, proteolytic enzyme inhibitors, integrase inhibitors and viral CCR5 co-receptor antagonists. In the past 20 years, highly active antiretroviral therapies (HAART) of the above drugs have been widely used in HIV-infected patients, which have greatly reduced the mortality rate of AIDS patients. However, AIDS is still an incurable disease, and a lot of challenges exist.

Non-nucleoside reverse transcriptase inhibitors (NNRTIs), characterized by high efficacy and low toxicity, having synergistic effects in combination with other drugs and diverse structures and et al., are important components of HARRT and have always been a hotspot in the research and development of anti-HIV-1 drugs. More than 60 types of NNRTIs have already been reported, and among them the S-dihydro-alkoxy-benzyl-oxopyrimidines (S-DABOs) type is a representative one. In the research of DABOs-type NNRTIs, a series of novel S-DACOs-type NNRTIs capable of inhibiting HIV replication at the nanomolar level have been discovered. Among them, the preferred compound DB02 has advantages such as significant anti-HIV efficacy, low toxicity and side effects, good prospects of drug combination and convenient synthesis. Nevertheless, the bioavailability of this compound is low due to its strong hydrophobicity, thereby affecting its druggability.

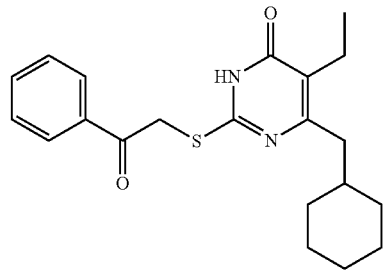

Content of the Disclosure

The technical problem to be solved by the present disclosure is to develop more novel non-nucleoside reverse transcriptase inhibitors (NNRTIs) of dihydro-alkoxy-benzyl-oxopyrimidines (DABOs), and thus a DACOs-type NNRTIs amino acid ester derivative, and a preparation method thereof, a pharmaceutical composition and a use thereof are provided herein. The DACOs-type NNRTIs amino acid ester derivative provided by the present disclosure is capable of acting as a HIV-1 inhibitor and can be used in the preparation of a medicament for treating and/or preventing immunodeficiency virus (HIV).

The present disclosure solves the above technical problem through the following technical solutions.

The present disclosure provides a DACOs-type NNRTIs amino acid ester derivative represented by formula I, or a tautomer, optical isomer, hydrate, solvate, polymorph, pharmaceutically acceptable salt or prodrug thereof:

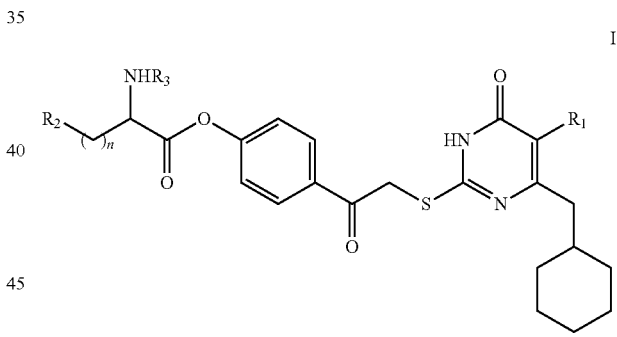

wherein:
$R_1$ is H, $C_1$-$C_6$ branched or straight chain alkyl, or $C_3$-$C_6$ cycloalkyl;
n is an integer between 0 and 8;
$R_2$ is H, $C_1$-$C_{12}$ straight or branched chain alkyl, $C_3$-$C_6$ cycloalkyl, —$C_1$-$C_{12}$ straight or branched chain alkyl-$NH_2$, —$C_1$-$C_{12}$ straight or branched chain alkyl-OH, $NH_2C$(=O)—, $C_1$-$C_{12}$ straight or branched chain alkoxy, $C_1$-$C_{12}$ straight or branched chain alkylthio, $C_6$-$C_{20}$ aryl, $C_2$-$C_{10}$ heteroaryl, $C_6$-$C_{20}$ aryl substituted by one or more (e.g., 1-6, preferably 1-3 or 1-2) $R_{2a}$, or $C_2$-$C_{10}$ heteroaryl substituted by one or more (e.g., 1-6, preferably 1-3 or 1-2) $R_{2b}$; wherein each of $R_{2a}$ and $R_{2b}$ is independently selected from hydroxyl, nitro, halogen, amino, cyano, sulfo group, $C_1$-$C_6$ branched or straight chain alkyl, $C_1$-$C_6$ branched or straight chain alkoxy, $C_1$-$C_6$ branched or straight chain alkylthio, $C_1$-$C_6$ branched or straight chain haloalkyl, and when the number of $R_{2a}$ or $R_{2b}$ is more, then each $R_{2a}$ or each $R_{2b}$ is the same or different.

$R_3$ is H, or $R_2$ and $R_3$ together with the structural fragment to which they are attached form $C_2$-$C_6$ heterocycloalkyl.

In the present disclosure, when $R_1$ is $C_1$-$C_6$ branched or straight chain alkyl, then the $C_1$-$C_6$ branched or straight chain alkyl is preferably $C_1$-$C_3$ branched or straight chain alkyl, more preferably isopropyl, n-propyl, ethyl or methyl;

when $R_1$ is $C_3$-$C_6$ cycloalkyl, then the $C_1$-$C_6$ cycloalkyl is preferably cyclopropyl, cyclobutyl, cyclopentyl or cyclohexyl;

in the present disclosure, n can be 0, 1, 2, 3, 4, 5, 6, 7 or 8.

In the present disclosure, when $R_2$ is $C_1$-$C_{12}$ branched or straight chain alkyl, then the $C_1$-$C_{12}$ branched or straight chain alkyl is preferably $C_1$-$C_6$ branched or straight chain alkyl, more preferably $C_1$-$C_4$ branched or straight chain alkyl, further more preferably methyl, ethyl, propyl, isopropyl, n-butyl, isobutyl, sec-butyl or tert-butyl;

when $R_2$ is $C_3$-$C_6$ cycloalkyl, then the $C_3$-$C_6$ cycloalkyl is preferably cyclopropyl, cyclobutyl, cyclopentyl or cyclohexyl;

when $R_2$ is —$C_1$-$C_{12}$ straight or branched chain alkyl-$NH_2$, then the $C_1$-$C_{12}$ straight or branched chain alkyl is preferably $C_1$-$C_6$ branched or straight chain alkyl, more preferably $C_1$-$C_4$ branched or straight chain alkyl, further more preferably methyl, ethyl, propyl, isopropyl, n-butyl, isobutyl, sec-butyl or tert-butyl;

when $R_2$ is —$C_1$-$C_{12}$ straight or branched chain alkyl-OH, then the $C_1$-$C_{12}$ straight or branched chain alkyl is preferably $C_1$-$C_6$ branched or straight chain alkyl, more preferably $C_1$-$C_4$ branched or straight chain alkyl, further more preferably methyl, ethyl, propyl, isopropyl, n-butyl, isobutyl, sec-butyl or tert-butyl;

when $R_2$ is $C_1$-$C_{12}$ straight or branched chain alkoxy, then the $C_1$-$C_{12}$ straight or branched chain alkoxy is preferably $C_1$-$C_6$ branched or straight chain alkoxy, more preferably $C_1$-$C_3$ branched or straight chain alkoxy, further more preferably methoxy, ethoxy, n-propoxy or isopropoxy;

when $R_2$ is $C_1$-$C_{12}$ straight or branched chain alkylthio, then the $C_1$-$C_{12}$ straight or branched chain alkylthio is preferably $C_1$-$C_6$ branched or straight chain alkylthio, more preferably $C_1$-$C_3$ branched or straight chain alkylthio, further more preferably methylthio, ethylthio, n-propylthio or isopropylthio;

when $R_2$ is $C_6$-$C_{20}$ aryl, then the $C_6$-$C_{20}$ aryl is preferably $C_6$-$C_{10}$ aryl, more preferably phenyl;

when $R_2$ is $C_2$-$C_{10}$ heteroaryl, then the $C_2$-$C_{10}$ heteroaryl is preferably $C_2$-$C_8$ heteroaryl, more preferably pyridyl, pyridazinyl, pyrimidinyl, pyrazinyl, furanyl, thienyl, pyrrolyl, pyrazolyl, indolyl, isoindolyl, imidazolyl, oxazolyl, isoxazolyl, thiazolyl, pyrimidinonyl, oxadiazolyl, pyridonyl or triazolyl;

when $R_2$ is $C_6$-$C_{20}$ aryl substituted by one or more $R_{2a}$, then the $C_6$-$C_{20}$ aryl is preferably $C_6$-$C_{10}$ aryl, more preferably phenyl;

when $R_2$ is $C_2$-$C_{10}$ heteroaryl substituted by one or more $R_{2b}$, then the $C_2$-$C_{10}$ heteroaryl is preferably $C_2$-$C_8$ heteroaryl, more preferably pyridyl, pyridazinyl, pyrimidinyl, pyrazinyl, furanyl, thienyl, pyrrolyl, pyrazolyl, indolyl, isoindolyl, imidazolyl, oxazolyl, isoxazolyl, thiazolyl, pyrimidinonyl, oxadiazolyl, pyridonyl or triazolyl.

In the present disclosure, when $R_2$ and $R_3$ together with the structural fragment to which they are attached form $C_2$-$C_6$ heterocycloalkyl, then the $C_2$-$C_6$ heterocycloalkyl is preferably azacyclohexyl, azacyclopentyl or azacyclobutyl.

In the present disclosure, when $R_{2a}$ or $R_{2b}$ is halogen, then the halogen is preferably fluorine, chlorine, bromine or iodine;

when $R_{2a}$ or $R_{2b}$ is $C_1$-$C_6$ branched or straight chain alkyl, then the $C_1$-$C_6$ branched or straight chain alkyl is preferably $C_1$-$C_3$ branched or straight chain alkyl, more preferably methyl, ethyl, n-propyl or isopropyl;

when $R_{2a}$ or $R_{2b}$ is $C_1$-$C_6$ branched or straight chain alkoxy, then the $C_1$-$C_6$ branched or straight chain alkoxy is preferably $C_1$-$C_3$ branched or straight chain alkoxy, more preferably methoxy, ethoxy, propoxy or isopropoxy;

when $R_{2a}$ or $R_{2b}$ is $C_1$-$C_6$ branched or straight chain alkylthio, then the $C_1$-$C_6$ branched or straight chain alkylthio is preferably $C_1$-$C_3$ branched or straight chain alkylthio, more preferably methylthio, ethylthio, propylthio or isopropylthio;

when $R_{2a}$ or $R_{2b}$ is $C_1$-$C_6$ branched or straight chain haloalkyl, then the $C_1$-$C_6$ branched or straight chain haloalkyl is $C_1$-$C_6$ branched or straight chain alkyl substituted by one or more same or different halogen atoms, the halogen atoms can be on the same or different carbon atoms; the $C_1$-$C_6$ branched or straight chain haloalkyl is preferably $C_1$-$C_3$ straight or branched chain haloalkyl, more preferably trifluoromethyl, difluoromethyl, or 1,2-difluoroethyl.

In the present disclosure, when $R_2$ is $C_2$-$C_{10}$ heteroaryl substituted by one or more $R_{2b}$, then the position through which the $C_2$-$C_{10}$ heteroaryl is connected to the rest of the DACOs-type NNRTIs amino acid ester derivative represented by formula I does not need to be particularly specified, preferably 2-position, 3-position or 4-position of the heteroaryl.

In a preferred embodiment of the present disclosure, $R_1$ is methyl, ethyl or isopropyl.

In a preferred embodiment of the present disclosure, $R_1$ is ethyl or isopropyl.

In a preferred embodiment of the present disclosure, n is 0, 1 or 2.

In a preferred embodiment of the present disclosure, $R_3$ is H.

In a preferred embodiment of the present disclosure, $R_2$ is H, $C_1$-$C_{12}$ straight or branched chain alkyl, —$C_1$-$C_{12}$ straight or branched chain alkyl-$NH_2$, $NH_2C(=O)$—, $C_1$-$C_{12}$ straight or branched chain alkoxy, $C_1$-$C_{12}$ straight or branched chain alkylthio, $C_6$-$C_{20}$ aryl, $C_2$-$C_{10}$ heteroaryl, $C_6$-$C_{20}$ aryl substituted by one or more (e.g., 1-6, preferably 1-3 or 1-2) $R_{2a}$ or $C_2$-$C_{10}$ heteroaryl substituted by one or more (e.g., 1-6, preferably 1-3 or 1-2) $R_{2b}$.

In a preferred embodiment of the present disclosure, $R_1$ is ethyl or isopropyl, n is 0, 1 or 2, $R_3$ is H, $R_2$ is H, $C_1$-$C_{12}$ straight or branched chain alkyl, —$C_1$-$C_{12}$ straight or branched chain alkyl-$NH_2$, $NH_2C(=O)$—, $C_1$-$C_{12}$ straight or branched chain alkoxy, $C_1$-$C_{12}$ straight or branched chain alkylthio, $C_6$-$C_{20}$ aryl or $C_2$-$C_{10}$ heteroaryl.

In a preferred embodiment of the present disclosure, $R_1$ is ethyl or isopropyl, n is 0, 1 or 2, $R_3$ is H, $R_2$ is H, isopropyl, isobutyl, sec-butyl or methylthio.

In a preferred embodiment of the present disclosure, the structural unit

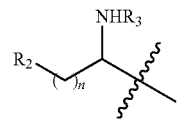

contained in the DACOs-type NNRTIs amino acid ester derivative represented by formula I is $NH_2$,

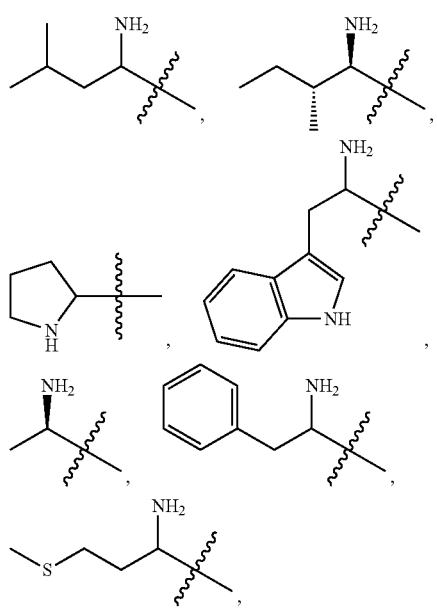,
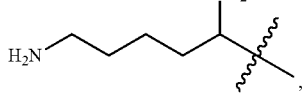,
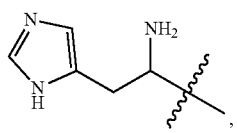       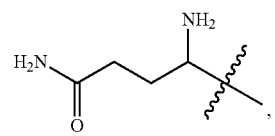,
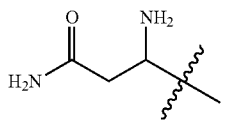  or  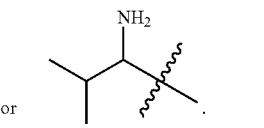.
In the present disclosure, the DACOs-type NNRTIs amino acid ester derivative represented by formula I is preferably a compound having any of the following structures:
| No. | Structure |
|---|---|
| I-1 | 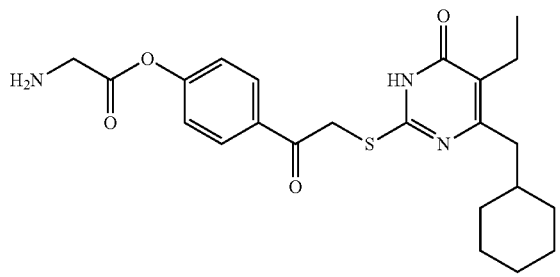 [SMILES: CCc1c(CC2CCCCC2)nc(SCC(=O)c2ccc(OC(=O)CN)cc2)[nH]c1=O] |
| I-2 | 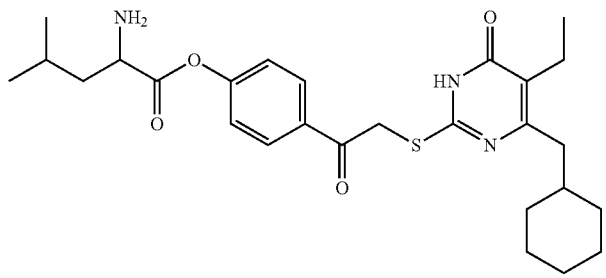 [SMILES: CCc1c(CC2CCCCC2)nc(SCC(=O)c2ccc(OC(=O)C(N)CC(C)C)cc2)[nH]c1=O] |
| I-3 | 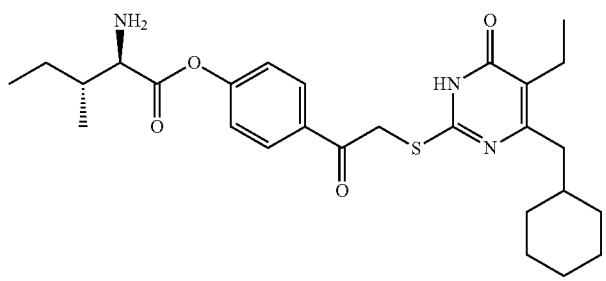 [SMILES: CCc1c(CC2CCCCC2)nc(SCC(=O)c2ccc(OC(=O)[C@H](N)[C@H](C)CC)cc2)[nH]c1=O] |

| No. | Structure |
|-----|-----------|
| I-4 | 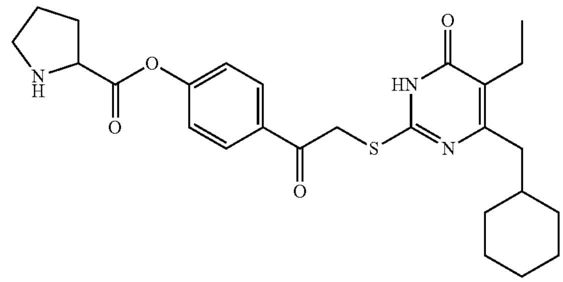 [SMILES: CCc1c(CC2CCCCC2)nc(SCC(=O)c2ccc(OC(=O)C3CCCN3)cc2)[nH]c1=O] |
| I-5 | 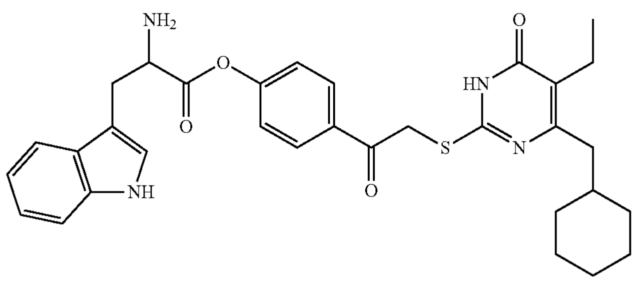 [SMILES: CCc1c(CC2CCCCC2)nc(SCC(=O)c2ccc(OC(=O)C(N)Cc3c[nH]c4ccccc34)cc2)[nH]c1=O] |
| I-6 | 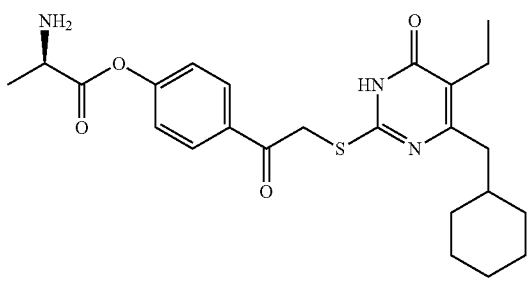 [SMILES: CCc1c(CC2CCCCC2)nc(SCC(=O)c2ccc(OC(=O)[C@@H](C)N)cc2)[nH]c1=O] |
| I-7 | 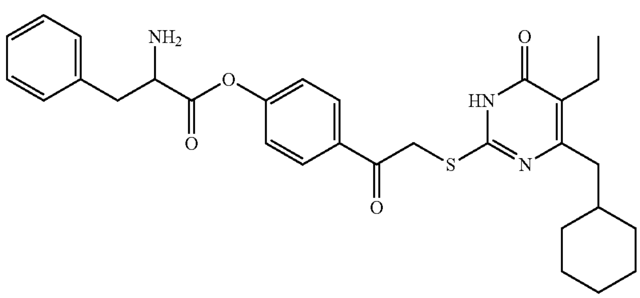 [SMILES: CCc1c(CC2CCCCC2)nc(SCC(=O)c2ccc(OC(=O)C(N)Cc3ccccc3)cc2)[nH]c1=O] |
| I-8 | 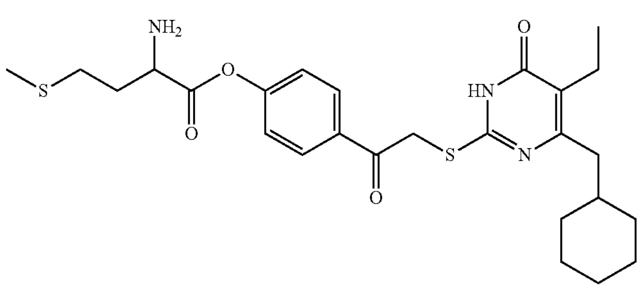 [SMILES: CCc1c(CC2CCCCC2)nc(SCC(=O)c2ccc(OC(=O)C(N)CCSC)cc2)[nH]c1=O] |

-continued

| No. | Structure |
|---|---|
| I-9 | 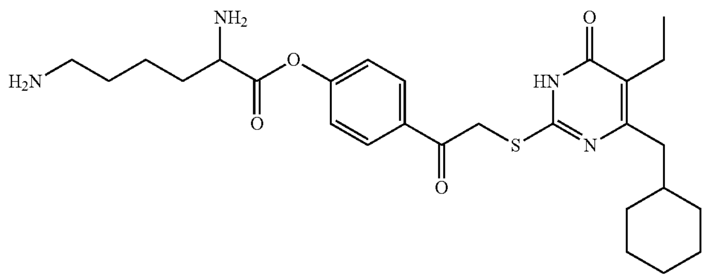 [SMILES: CCc1c(CC2CCCCC2)nc(SCC(=O)c2ccc(OC(=O)C(N)CCCCN)cc2)[nH]c1=O] |
| I-10 | 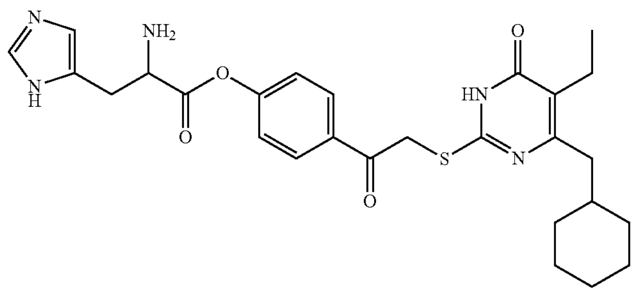 [SMILES: CCc1c(CC2CCCCC2)nc(SCC(=O)c2ccc(OC(=O)C(N)Cc3cnc[nH]3)cc2)[nH]c1=O] |
| I-11 | 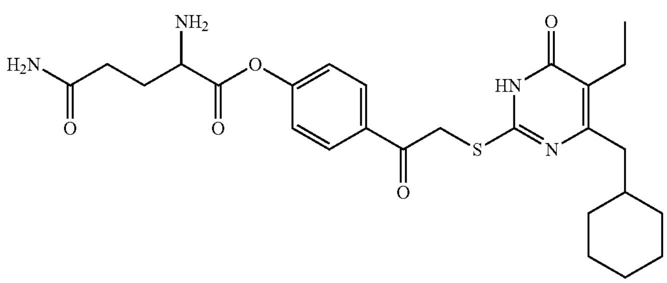 [SMILES: CCc1c(CC2CCCCC2)nc(SCC(=O)c2ccc(OC(=O)C(N)CCC(N)=O)cc2)[nH]c1=O] |
| I-12 | 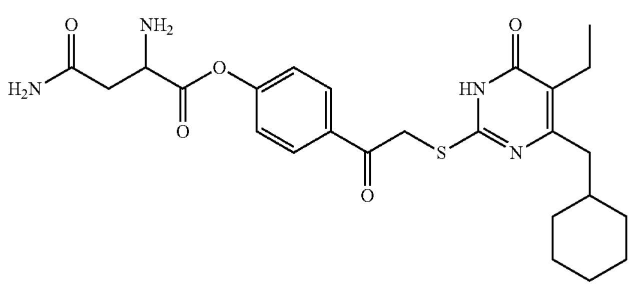 [SMILES: CCc1c(CC2CCCCC2)nc(SCC(=O)c2ccc(OC(=O)C(N)CC(N)=O)cc2)[nH]c1=O] |
| I-13 | 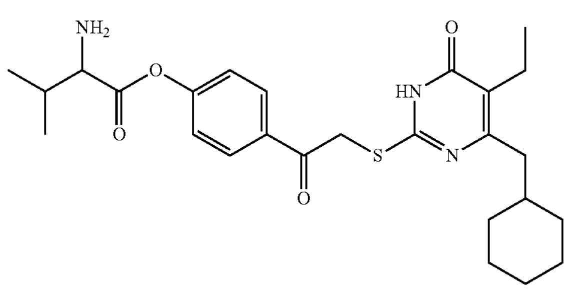 [SMILES: CCc1c(CC2CCCCC2)nc(SCC(=O)c2ccc(OC(=O)C(N)C(C)C)cc2)[nH]c1=O] |

| No. | Structure |
|---|---|
| I-14 | 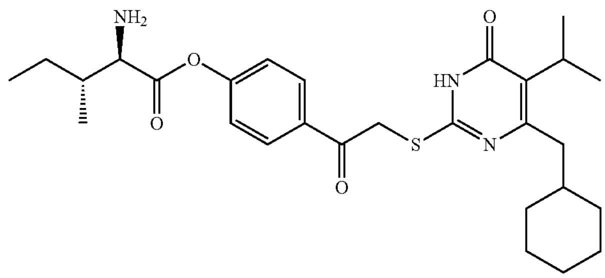 [SMILES: CC[C@@H](C)[C@@H](N)C(=O)Oc1ccc(C(=O)CSc2nc(CC3CCCCC3)c(C(C)C)c(=O)[nH]2)cc1] |
| I-15 | 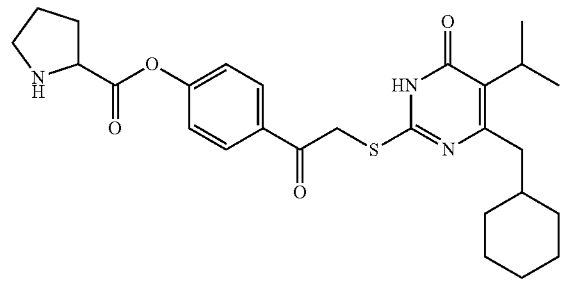 [SMILES: CC(C)c1c(CC2CCCCC2)nc(SCC(=O)c2ccc(OC(=O)C3CCCN3)cc2)[nH]c1=O] |
| I-16 | 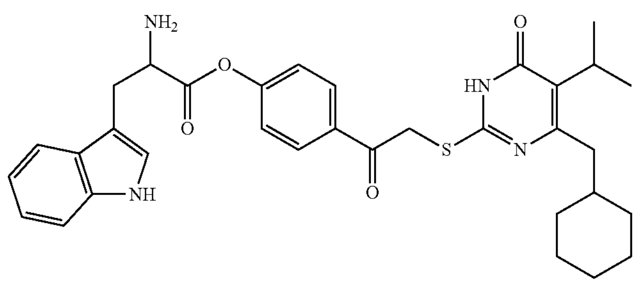 [SMILES: CC(C)c1c(CC2CCCCC2)nc(SCC(=O)c2ccc(OC(=O)C(N)Cc3c[nH]c4ccccc34)cc2)[nH]c1=O] |
| I-17 | 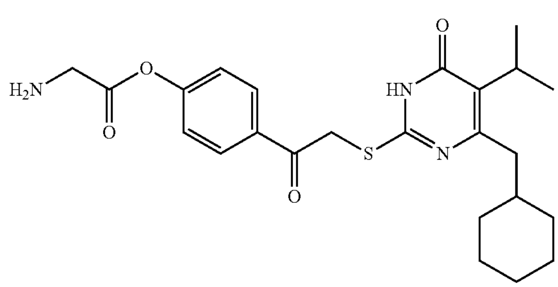 [SMILES: CC(C)c1c(CC2CCCCC2)nc(SCC(=O)c2ccc(OC(=O)CN)cc2)[nH]c1=O] |
| I-18 | 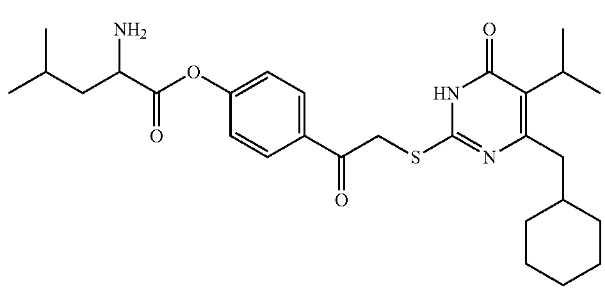 [SMILES: CC(C)CC(N)C(=O)Oc1ccc(C(=O)CSc2nc(CC3CCCCC3)c(C(C)C)c(=O)[nH]2)cc1] |

-continued

| No. | Structure |
|-----|-----------|
| I-19 | 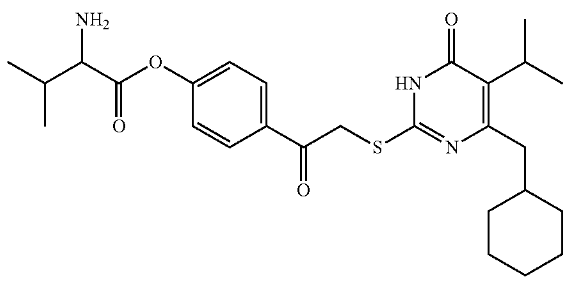 [SMILES: CC(C)c1c(CC2CCCCC2)nc(SCC(=O)c2ccc(OC(=O)C(N)C(C)C)cc2)[nH]c1=O] |
| I-20 | 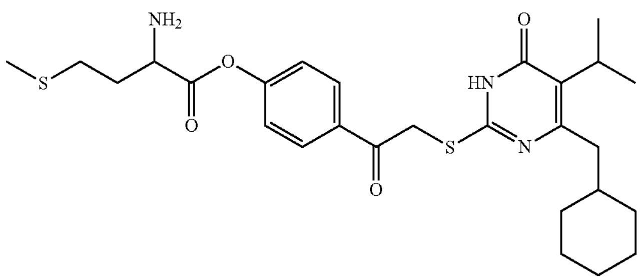 [SMILES: CSCCC(N)C(=O)Oc1ccc(C(=O)CSc2nc(CC3CCCCC3)c(C(C)C)c(=O)[nH]2)cc1] |
| I-21 | 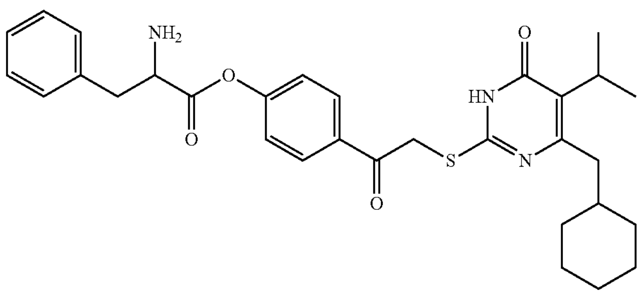 [SMILES: CC(C)c1c(CC2CCCCC2)nc(SCC(=O)c2ccc(OC(=O)C(N)Cc3ccccc3)cc2)[nH]c1=O] |
| I-22 | 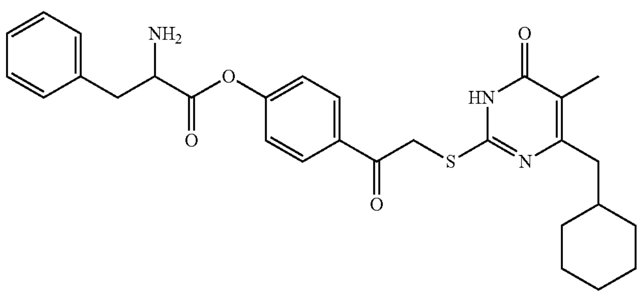 [SMILES: Cc1c(CC2CCCCC2)nc(SCC(=O)c2ccc(OC(=O)C(N)Cc3ccccc3)cc2)[nH]c1=O] |
| I-23 | 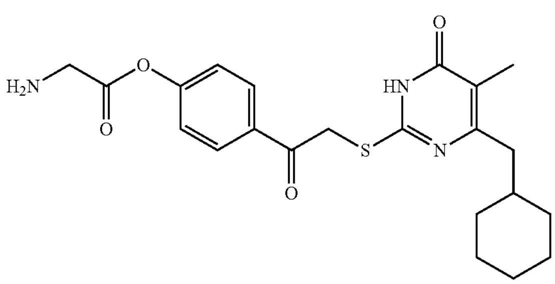 [SMILES: Cc1c(CC2CCCCC2)nc(SCC(=O)c2ccc(OC(=O)CN)cc2)[nH]c1=O] |

| No. | Structure |
|---|---|
| I-24 | 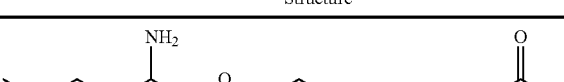 |

The present disclosure also provides a method for preparing the DACOs-type NNRTIs amino acid ester derivative represented by formula I, which comprises carrying out a Boc removal reaction of intermediate 6 in the presence of an acidic reagent in a solvent;

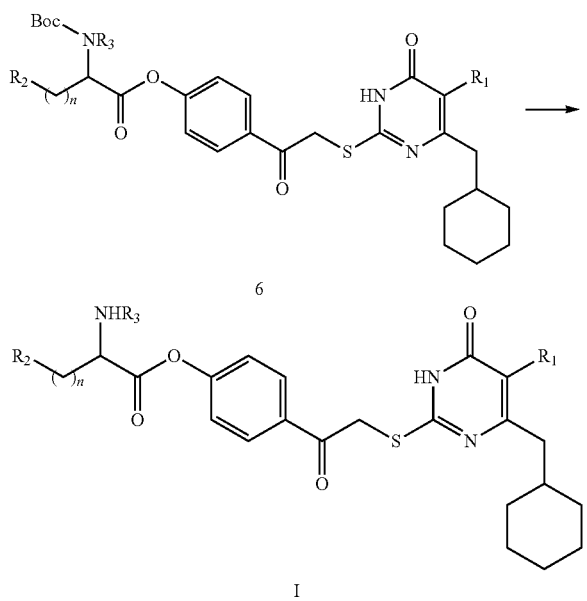

wherein the definitions of n, $R_1$, $R_2$ and $R_3$ are as defined above.

In the present disclosure, the Boc removal reaction occurs in accordance with the mechanism of this type of Boc removal reaction in the art, and conventional conditions and parameters for this type of Boc removal reaction in the art can be employed.

In the present disclosure, the solvent can be a conventional solvent for this type of reaction in the art, which does not participate in or interfere with the reaction, and the solvent is preferably one or more selected from dichloromethane, chloroform, ethyl acetate, acetonitrile and tetrahydrofuran.

In the present disclosure, the amount of the solvent can be a conventional amount for this type of reaction in the art, which is sufficient for completely dissolving the reactants and ensuring the smooth progress of the reaction.

In the present disclosure, the acidic reagent can be a conventional acidic reagent for this type of reaction in the art, which is preferably one or more selected from hydrochloric acid, sulfuric acid and acetic acid in the present disclosure.

In the present disclosure, the amount of the acidic reagent can be a conventional amount for this type of reaction in the art and can be excess. In the present disclosure, the amount of which is not particularly limited.

In the present disclosure, the reaction temperature of the Boc removal reaction can be a conventional temperature for this type of reaction in the art, which is preferably controlled between 10 and 50° C., e.g., room temperature (20-25° C.).

In the present disclosure, the progress of the Boc removal reaction can be monitored by conventional detection methods in the art (e.g., TLC, HPLC or NMR), and the point where a raw material disappears or does not proceed to react is generally seen as completion of the reaction. The reaction time of the Boc removal reaction is preferably 0.5-4 hours, more preferably 1-2 hours.

In the present disclosure, the method for preparing the DACOs-type NNRTIs amino acid ester derivative represented by formula I preferably comprises dissolving the intermediate 6 in the solvent, adding the acidic reagent and reacting at room temperature under stirring.

In the present disclosure, after the completion of the Boc removal reaction, the method for preparing the DACOs-type NNRTIs amino acid ester derivative represented by formula I preferably comprises a post-treatment step comprising: neutralizing the reaction solution by addition of saturated sodium carbonate solution until the reaction is no longer vigorous after the completion of the Boc removal reaction, further neutralizing with saturated sodium bicarbonate solution until no bubble is generated, filtering the mixture to obtain the precipitate as a crude product of the target product and recrystallizing.

In the present disclosure, the method for preparing the DACOs-type NNRTIs amino acid ester derivative represented by formula I preferably further comprises carrying out an alkylation reaction of intermediate 4 and intermediate 5 in the presence of a weakly basic reagent in a solvent to obtain the intermediate 6;

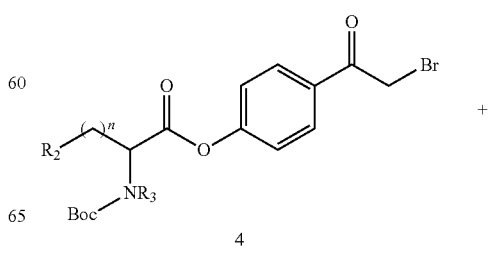

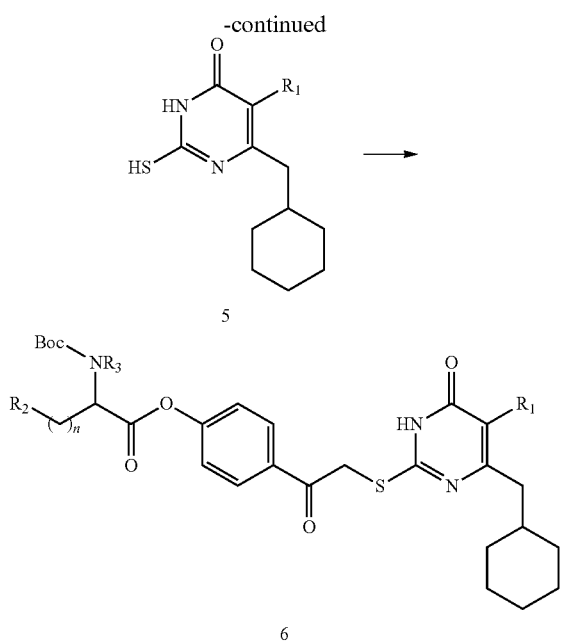

wherein the definitions of n, $R_1$, $R_2$ and $R_3$ are as defined above.

In the present disclosure, the alkylation reaction occurs in accordance with the mechanism of this type of alkylation reaction in the art, and conventional conditions and parameters for this type of alkylation reaction in the art can be employed.

In the present disclosure, the solvent can be a conventional solvent for this type of reaction in the art, which does not participate in or interfere with the reaction, and the solvent is preferably one or more selected from DMF, pyridine, dichloromethane, acetonitrile and tetrahydrofuran, more preferably DMF.

In the present disclosure, the amount of the solvent can be a conventional amount for this type of reaction in the art, which is sufficient for completely dissolving the reactants and ensuring the smooth progress of the reaction.

In the present disclosure, the weakly basic reagent can be a conventional weakly basic reagent for this type of reaction in the art, which is preferably one or more selected from $K_2CO_3$, $NaHCO_3$ and $Et_3N$.

In the present disclosure, the amount of the weakly basic reagent can be a conventional amount for this type of reaction in the art, and the molar ratio of the intermediate to the weakly basic reagent is preferably 1:1 to 1:1.5, e.g., 1:1.2.

In the present disclosure, the molar ratio of the intermediate 5 to the intermediate 4 can be a conventional ratio for this type of reaction in the art, which is preferably 1:1 to 1:1.5, e.g., 1:1.1 to 1:1.2.

In the present disclosure, the reaction temperature of the alkylation reaction can be a conventional temperature for this type of reaction in the art, which is preferably controlled between 20 and 80° C., e.g., room temperature (20-25° C.).

In the present disclosure, the progress of the alkylation reaction can be monitored by conventional detection methods in the art (e.g., TLC, HPLC or NMR), and the point where a raw material disappears or does not proceed to react is generally seen as completion of the reaction. The reaction time of the alkylation reaction is preferably 3-24 hours.

In the present disclosure, the method for preparing the DACOs-type NNRTIs amino acid ester derivative represented by formula I preferably comprises dissolving the intermediate 5 in part of the solvent, adding the weakly basic reagent, then adding a solution of the intermediate 4 in the remaining part of the solvent after stirring, and reacting under continuous stirring.

In the present disclosure, after the completion of the alkylation reaction, the method for preparing the DACOs-type NNRTIs amino acid ester derivative represented by formula I preferably comprises a post-treatment step comprising pouring the reaction solution into ice water after the completion of the alkylation reaction, vigorously stirring the mixture with white turbidity generated, extracting with ethyl acetate, combining the organic layers and evaporating the solvent under reduced pressure to obtain a crude product.

In the present disclosure, the intermediate 5 can be prepared by a method well known to those skilled in the organic chemistry field, Yan-Ping He, Jin Long, et al., *Bioorg. & Med. Chem.* 2011, 21, 694-697, third paragraph on page 695 and Zhi-Kun Rao, Jing Long, et al., *Monatsh Chem.* 2008, 139, 967-974 can be referred to for details (the contents of these references are incorporated herein by reference), specific synthetic routes are shown below:

Method 1

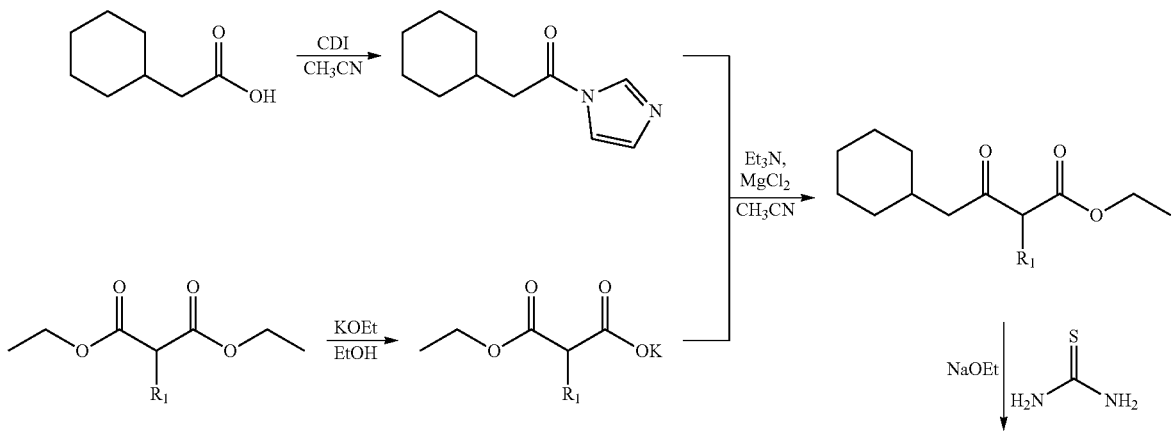

-continued

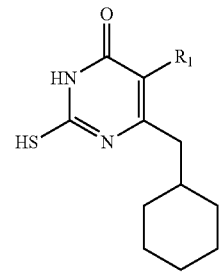

Method 2

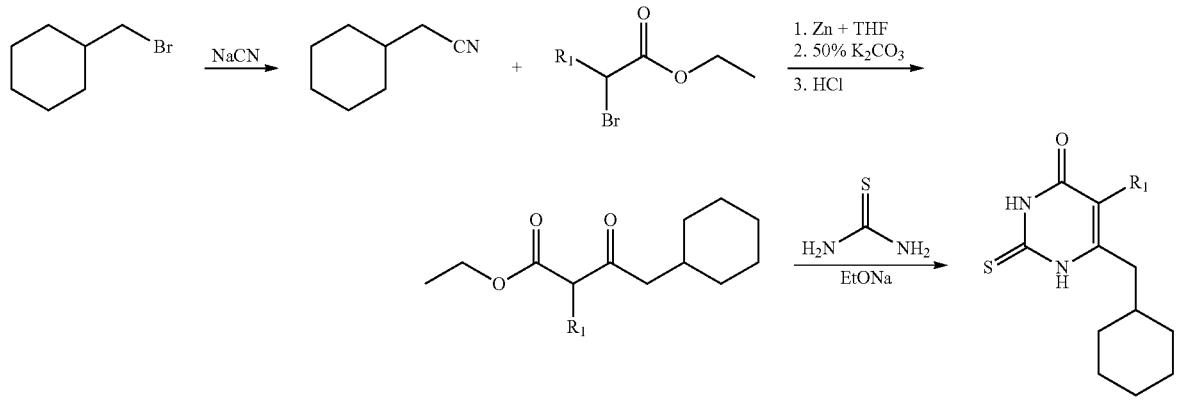

wherein the definition of $R_1$ is as defined above.

In the present disclosure, the method for preparing the DACOs-type NNRTIs amino acid ester derivative represented by formula I preferably further comprises carrying out a condensation reaction of intermediate 2 and intermediate 3 in the presence of a catalyst and a condensing agent in a solvent to obtain the intermediate 4;

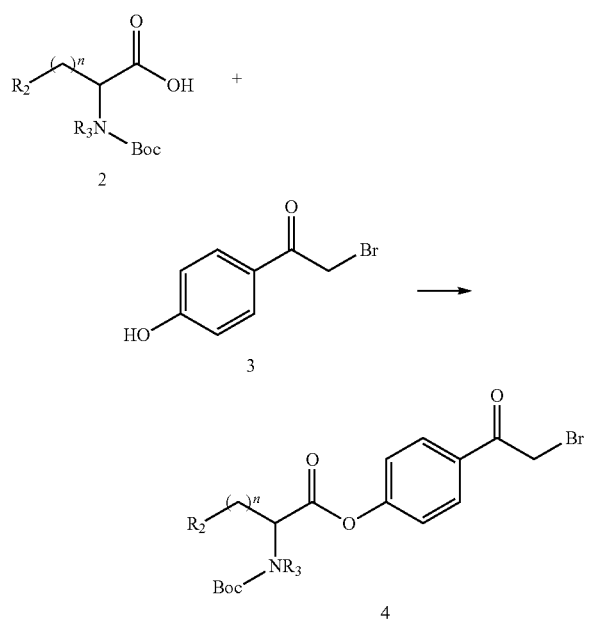

wherein the definitions of n, $R_2$ and $R_3$ are as defined above.

In the present disclosure, the condensation reaction occurs in accordance with the mechanism of this type of condensation reaction in the art, and conventional conditions and parameters for this type of condensation reaction in the art can be employed.

In the present disclosure, the solvent can be a conventional solvent for this type of reaction in the art, which does not participate in or interfere with the reaction, and the solvent is preferably dichloromethane.

In the present disclosure, the amount of the solvent can be a conventional amount for this type of reaction in the art, which is sufficient for completely dissolving the reactants and ensuring the smooth progress of the reaction.

In the present disclosure, the molar ratio of the intermediate 2 to the intermediate 3 can be a conventional ratio for this type of reaction in the art, which is preferably 1:1 to 1:3, e.g., 1:1.1.

In the present disclosure, the catalyst can be a conventional catalyst for this type of reaction in the art, which is preferably DMAP.

In the present disclosure, the amount of the catalyst can be a conventional amount for this type of reaction in the art, and the molar ratio of the intermediate 2 to the catalyst is preferably 1:0.01 to 1:0.2.

In the present disclosure, the condensing agent can be a conventional condensing agent for this type of reaction in the art, which is preferably DCC.

In the present disclosure, the amount of the condensing agent can be a conventional amount for this type of reaction in the art; and the molar ratio of the intermediate 2 to the condensing agent is preferably 1:1 to 1:1.2.

In the present disclosure, the reaction temperature of the condensation reaction can be a conventional temperature for this type of reaction in the art, which is preferably controlled between 0 and 60° C.

In the present disclosure, the progress of the condensation reaction can be monitored by conventional detection methods in the art (e.g., TLC, HPLC or NMR), and the point where a raw material disappears or does not proceed to react is generally seen as completion of the reaction. The reaction time of the condensation reaction is preferably 2-12 hours.

In the present disclosure, the method for preparing the DACOs-type NNRTIs amino acid ester derivative represented by formula I preferably comprises adding the condensing agent and the catalyst to a mixture of the intermediate 2 and the solvent, stirring under a condition of ice bath, adding the intermediate 3 slowly, and stirring at room temperature to carry out the condensation reaction.

In the present disclosure, after the completion of the condensation reaction, the method for preparing the DACOs-type NNRTIs amino acid ester derivative represented by formula I preferably comprises a post-treatment step comprising suction filtration after the completion of the condensation reaction, then concentrating the filtrate under reduced pressure and purifying the concentrate by column chromatography to obtain the intermediate 4.

In the present disclosure, the method for preparing the DACOs-type NNRTIs amino acid ester derivative represented by formula I preferably further comprises carrying out a N-Boc protection reaction of intermediate 1 with $(Boc)_2O$ in the presence of a base in a solvent to obtain the intermediate 2;

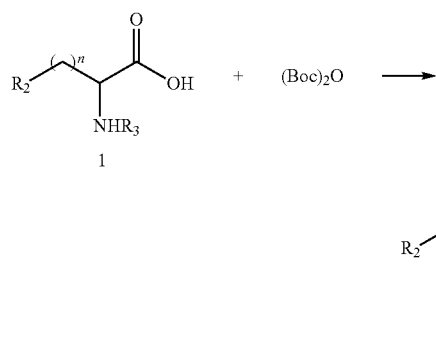

wherein the definitions of n, $R_2$ and $R_3$ are as defined above.

In the present disclosure, the N-Boc protection reaction occurs in accordance with the mechanism of this type of N-Boc protection reaction in the art, and conventional conditions and parameters for this type of N-Boc protection reaction in the art can be employed.

In the present disclosure, the solvent can be a conventional solvent for this type of reaction in the art, which does not participate in or interfere with the reaction, and the solvent is preferably one or more selected from DMSO, DMF, water, dioxane and acetonitrile, more preferably a mixed solvent of dioxane and water (2:1, v/v).

In the present disclosure, the amount of the solvent can be a conventional amount for this type of reaction in the art, which is sufficient for completely dissolving the reactants and ensuring the smooth progress of the reaction.

In the present disclosure, the base can be a strong base conventionally used in this type of reaction in the art, e.g., sodium hydroxide.

In the present disclosure, the amount of the base can be a conventional amount for this type of reaction in the art, and the molar ratio of the intermediate 1 to the base is preferably 1:1 to 1:2.

In the present disclosure, the molar ratio of the intermediate 1 to $(Boc)_2O$ can be a conventional ratio for this type of reaction in the art, which is preferably 1:2 to 1:4.

In the present disclosure, the reaction temperature of the N-Boc protection reaction can be a conventional temperature for this type of reaction in the art, which is preferably controlled between 10 and 50° C.

In the present disclosure, the progress of the N-Boc protection reaction can be monitored by conventional detection methods in the art (e.g., TLC, HPLC or NMR), and the point where a raw material disappears or does not proceed to react is generally seen as completion of the reaction. The reaction time of the N-Boc protection reaction is preferably 6-24 hours, more preferably 10-12 hours.

In the present disclosure, the method for preparing the DACOs-type NNRTIs amino acid ester derivative represented by formula I preferably comprises slowly adding the base into a mixture of the intermediate 2 and the solvent, adding the $(Boc)_2O$ after stirring, and stirring overnight.

In the present disclosure, after the completion of the N-Boc protection reaction, the method for preparing the DACOs-type NNRTIs amino acid ester derivative represented by formula I preferably comprises a post-treatment step comprising evaporating the solvent after the completion of the condensation reaction, adjusting the pH to about 3 with 1N HCl, extracting with ethyl acetate, combining the organic layers, drying over anhydrous $Na_2SO_4$, removing the solvent under reduced pressure to obtain a colorless oily liquid, adding a mixed solvent of ethyl ether and petroleum ether (8:1, v/v), vigorously stirring to obtain a white solid, filtering by suction and drying to obtain the intermediate 2.

In the present disclosure, the method for preparing the DACOs-type NNRTIs amino acid ester derivative represented by formula I preferably employs the following synthetic route:

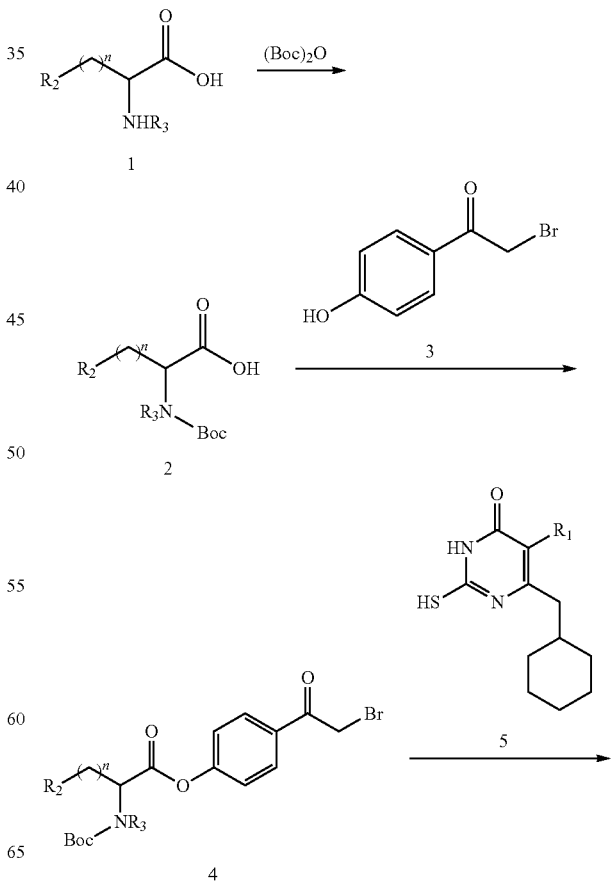

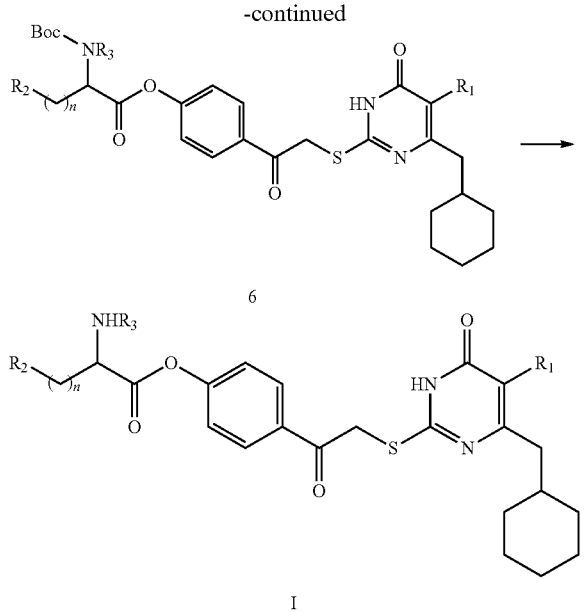

wherein the definitions of n, $R_1$, $R_2$ and $R_3$ are as defined above, the specific reaction conditions and parameters for each reaction of each step are as described above.

According to the preparation method described above, those skilled in the art can employ the same principle and method to prepare each specific compound involved in the general formula I of the present disclosure.

The present disclosure also provides a use of the DACOs-type NNRTIs amino acid ester derivative represented by formula I, the tautomer, optical isomer, hydrate, solvate, polymorph, pharmaceutically acceptable salt or prodrug thereof as a non-nucleoside HIV-1 inhibitor, and the non-nucleoside HIV-1 inhibitor is preferably a non-nucleoside HIV-1$_{IIIB}$ inhibitor.

The present disclosure also provides a use of the DACOs-type NNRTIs amino acid ester derivative represented by formula I, the tautomer, optical isomer, hydrate, solvate, polymorph, pharmaceutically acceptable salt or prodrug thereof in the manufacture of an anti-HIV-1 medicament.

The present disclosure also provides a use of the DACOs-type NNRTIs amino acid ester derivative represented by formula I, the tautomer, optical isomer, hydrate, solvate, polymorph, pharmaceutically acceptable salt or prodrug thereof in the manufacture of a medicament for treating and/or preventing human immunodeficiency virus (HIV) infection.

The present disclosure also provides a pharmaceutical composition comprising a therapeutically effective amount of the DACOs-type NNRTIs amino acid ester derivative represented by formula I, the tautomer, optical isomer, hydrate, solvate, polymorph, pharmaceutically acceptable salt or prodrug thereof, and at least one pharmaceutical excipient. The mass percentage of the DACOs-type NNRTIs amino acid ester derivative represented by formula I, the tautomer, optical isomer, hydrate, solvate, polymorph, pharmaceutically acceptable salt or prodrug thereof in the pharmaceutical composition is 0.1% to 99.9%, and the mass percentage refers to the mass of the DACOs-type NNRTIs amino acid ester derivative represented by formula I, the tautomer, optical isomer, hydrate, solvate, polymorph, pharmaceutically acceptable salt or prodrug thereof in the total mass of pharmaceutical composition. The sum of the mass fractions of the DACOs-type NNRTIs amino acid ester derivative represented by formula I, the tautomer, optical isomer, hydrate, solvate, polymorph, pharmaceutically acceptable salt or prodrug thereof and the pharmaceutical excipient is 100%. The selection of the pharmaceutical excipient varies with the route of administration and the characteristics of the action, and is generally a filler, a diluent, a binder, a wetting agent, a disintegrant, a lubricant, an emulsifier or a suspending agent.

The present disclosure also provides a method for treating human immunodeficiency virus (HIV) infection disease, wherein the method comprises administering a therapeutically effective amount of the DACOs-type NNRTIs amino acid ester derivative represented by formula I, the tautomer, optical isomer, hydrate, solvate, polymorph, pharmaceutically acceptable salt or prodrug thereof to a subject in need thereof.

Unless otherwise specified, the following terms employed in the description and the claims of the present disclosure have the following meanings.

The term "pharmaceutically acceptable salt" refers to a salt of the compound of the present disclosure which is prepared by reacting the compound of the present disclosure having a specific substituent with a relatively non-toxic acid or base. When the compound of the present disclosure contains a relatively acidic functional group, a base addition salt can be obtained by contacting the neutral form of the compound with a sufficient amount of a base in a pure solution or a suitable inert solvent. The pharmaceutically acceptable base addition salt includes a salt of sodium, potassium, calcium, ammonium, organic amine or magnesium or similar salts. When the compound of the present disclosure contains a relatively basic functional group, an acid addition salt can be obtained by contacting the neutral form of the compound with a sufficient amount of an acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, etc.; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzene sulfonic acid, p-toluenesulfonic acid, citric acid, tartaric acid, and methanesulfonic acid, etc.; and an salt of amino acid (e.g., arginine), and a salt of an organic acid such as glucuronic acid (referring to Berge et al., "Pharmaceutical Salts", *Journal of Pharmaceutical Science* 66: 1-19 (1977), the contents of which are incorporated herein by reference in its entirety). Certain specific compounds of the present disclosure which contain both basic and acidic functional groups can be converted to any base or acid addition salt.

Preferably, through contacting a salt with a base or an acid in a conventional manner, then separating the parent compound, the neutral form of the compound is thereby regenerated. The difference between the parent form of the compound and its various salt forms lies in specific physical properties, such as different solubility in a polar solvent.

"Pharmaceutically acceptable salt" used herein belongs to a derivative of the compound of the present disclosure, wherein the parent compound is modified by forming a salt with an acid or a base. Examples of the pharmaceutically acceptable salt include but are not limited to an inorganic acid or organic acid salt of a basic moiety such as amine, an alkali metal salt or an organic salt of an acidic moiety such as carboxylic acid, and the like. The pharmaceutically acceptable salt includes conventional non-toxic salt or quaternary ammonium salt of the parent compound, such as a salt formed by a non-toxic inorganic acid or an organic acid. The conventional non-toxic salt includes but is not limited to the salt derived from an inorganic acid and an organic acid, wherein the inorganic acid or organic acid is selected from 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactanal acid, propionic acid, salicylic acid, stearic acid, subacetic acid, succinic acid, sulfamic acid, sulfanilic acid, sulfuric acid, tannin, tartaric acid and p-toluenesulfonic acid.

The pharmaceutically acceptable salt of the present disclosure can be prepared from the parent compound which contains an acidic or basic moiety by conventional chemical methods. Generally, such salt can be prepared by reacting the free acid or base form of the compound with a stoichiometric amount of an appropriate base or acid in water or an organic solvent or a mixture thereof. Generally, a non-aqueous medium, e.g., an ether, ethyl acetate, ethanol, isopropanol or acetonitrile, is preferred.

In addition to the salt form, the compound provided by the present disclosure also exists in the prodrug form. The prodrug of the compound described herein is a compound that readily undergoes chemical change under physiological condition to be converted into the compound of the present disclosure. Additionally, the prodrug can be converted to the compound of the present disclosure by a chemical or biochemical method in vivo environment.

Some compounds of the present disclosure can exist in the unsolvated or solvated form, including hydrated form. Generally speaking, the solvated form is equivalent to the unsolvated form, and both are included within the scope of the present disclosure. Some compounds of the present disclosure can exist in the polymorphous form or amorphous form.

The term "pharmaceutically acceptable carrier" refers to a carrier for any preparation or carrier medium which can deliver an effective amount of the active substances of the present disclosure, does not interfere with the biological activity of the active substances and has no toxic side effects on hosts or patients, representative carries includes water, oil, vegetable and mineral, paste, lotion matrix, ointment matrix, etc. These matrices include suspensions, tackifiers, penetration enhancers, etc. Their preparations are well known to those skilled in the art of cosmetics or topical pharmaceuticals. For other information about carriers, *Remington: The Science and Practice of Pharmacy,* 21st Ed., Lippincott, Williams & Wilkins (2005), which is incorporated herein by reference, can be referred to.

The term "excipient" usually refers to a carrier, a diluent and/or a medium required for the preparation of an effective pharmaceutical composition.

For pharmaceuticals or pharmacological active agents, the term "effective amount" or "therapeutic effective amount" refers to an amount of a drug or medicament that is non-toxic but is sufficient to achieve the desired effect. For the oral dosage form in the present disclosure, the "effective amount" of an active substance in the composition refers to an amount required to achieve the desired effect when combined with another active substance in the composition. The determination of the effective amount varies from person to person, depending on age and general condition of a receptor, and also on a specific active substance. The appropriate effective amount in a case can be determined by those skilled in the art according to routine experiments.

Some compounds of the present disclosure can contain asymmetric carbon atoms (optical center) or double bonds. Racemic isomers, diastereomers, geometric isomers and single isomers are all encompassed within the scope of the present disclosure.

The compound of the present disclosure can have a specific geometric or stereoisomeric form. The present disclosure contemplates all of such compounds, including cis and trans isomers, (−)- and (+)-enantiomers, (R)- and (S)-enantiomers, diastereoisomers, (D)-isomers, (L)-isomers, and racemic mixtures and other mixtures, for example, enantiomer or diastereoisomer enriched mixtures, are encompassed within the scope of the present disclosure. Substituents such as alkyl can have an additional asymmetric carbon atom. All these isomers and mixtures thereof are encompassed within the scope of the present disclosure.

The diagrammatic representation of racemic isomer, ambiscalemic and scalemic or enantiopure compound of the present disclosure is from Maehr, *J. Chem. Ed.* 1985, 62: 114-120. Unless otherwise indicated, the absolute configuration of a stereocenter is represented by wedged and dashed lines. When the compound of the present disclosure contains a vinyl double bond or other geometric asymmetric center, unless otherwise specified, E, Z geometric isomers are included. Similarly, all tautomeric forms are encompassed within the scope of the present disclosure.

The chemical general formula involved in the present disclosure can exhibit tautomerism, structural isomerism and stereoisomerism. The present disclosure includes any tautomeric or structural isomeric or stereoisomeric form and a mixture thereof, and they have the ability to modulate kinase activity which is not limited to any form of the isomer or the mixture thereof.

Optically active (R)- and -isomers, (D)- and (L)-isomers can be prepared by chiral synthesis or chiral reagents or other conventional techniques. If an enantiomer of a compound of the present disclosure is desired, asymmetric synthesis or derivatization action of the chiral auxiliaries can be employed in preparation, in which the resulting diastereomer mixtures are isolated, and the auxiliary groups are cleaved to provide the pure desired enantiomer. Alternatively, when a molecule contains a basic functional group (e.g., amino) or an acidic functional group (e.g., carboxyl), a salt of a diastereomer is formed with an appropriate optical active acid or base, and then the pure enantiomer can be recycled after resolution on the salt of diastereomer by methods well known in the art. In addition, the isolation of an enantiomer and a diastereomer is usually realized by a chromatographic method, the chromatography method employs a chiral stationary phase, optionally in combination with a chemical derivatization method (e.g., an amine generates a carbamate).

One or more atoms constituting the compound of the present disclosure can comprise an unnatural proportion of atomic isotopes. For example, the compound can be labeled by a radioactive isotope, e.g., tritium ($^3H$), iodine-125 ($^{125}I$) or C-14 ($^{14}C$). All of these variations in the isotopic composition of the compound of the present disclosure, whether radioactive or not, are encompassed within the scope of the present disclosure.

Unless otherwise specified, the reagents and raw materials used in the present disclosure are commercially available.

Unless otherwise specified, compounds are named manually or by ChemDraw® software, commercially available compounds use their vendor directory names.

In accordance with common knowledge in the art, the above-mentioned preferred conditions can be arbitrarily combined to obtain preferred embodiments of the present disclosure.

The advantageous effect of the present disclosure is that the present disclosure provides a novel amino acid ester derivative of DACOs, and a preparation method, pharmaceutical composition and use thereof. Tests have proved that the amino acid ester derivative of DACOs provided by the present disclosure can be used as a HIV-1 inhibitor and has high use value. Specifically, the amino acid ester derivative of DACOs can be used in the preparation of an anti-AIDS medicament as a HIV-1 inhibitor. The DACOs-type NNRTIs amino acid ester derivative provided by the present disclosure has significant anti-HIV activity and superior pharmacokinetic property (ADME) compared with DB02 as indicated by calculation with molinspiration software.

DETAILED DESCRIPTION OF THE EMBODIMENT

The following describes the present disclosure in detail with embodiments, but it does not impose any adverse limitation on the present disclosure. The present disclosure has been described in detail herein, and its specific embodiments are also disclosed. It is obvious to those skilled in the art that various changes and improvements can be made to the specific embodiments of the present disclosure without departing from the spirit and scope of the present disclosure.

The experimental methods which are not specified in the following examples are selected according to conventional methods and conditions, or according to product specifications. The raw materials can be obtained from commercial sources, or prepared by methods known in the art, or prepared according to the methods described herein. The structures of the compounds were determined by nuclear magnetic resonance ($^1H$ NMR or $^{13}C$ NMR) or mass spectrometry (MS), wherein NMR was measured by Bruker AV-300 type nuclear magnetic resonance instrument with deuterated dimethyl sulfoxide (DMSO-D6) or deuterated chloroform (CDCl$_3$) as the solvent and TMS as the internal standard.

Preparation Example 1: Preparation of the Target Compound I

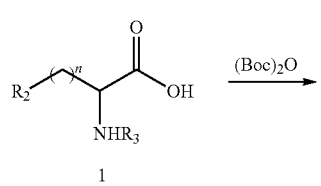

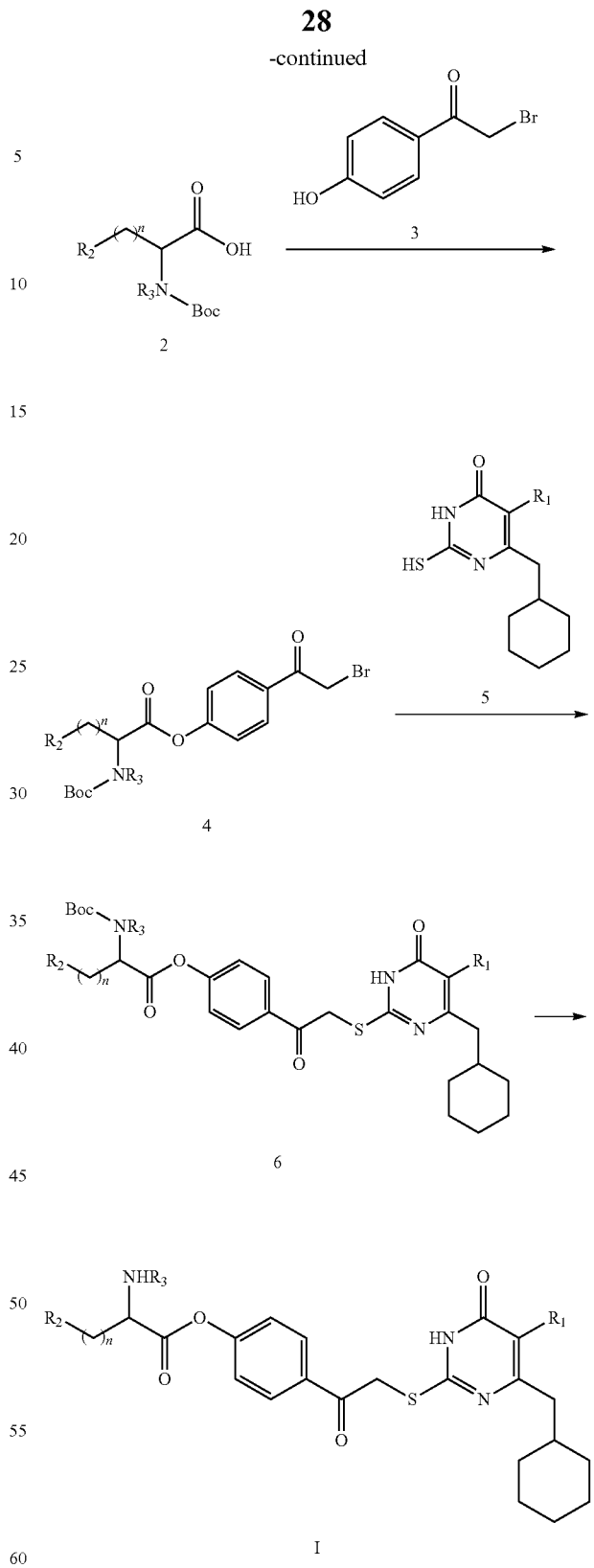

The preparation method of substituted thiouracil 5 was as follows (referring to Yan-Ping He, Jin Long, et al. *Bioorg. & Med. Chem.* 2011, 21, 694-697; Zhi-Kun Rao, Jing Long, et al. *Monatsh Chem.* 2008, 139, 967-974, the contents of these references are incorporated herein by reference).

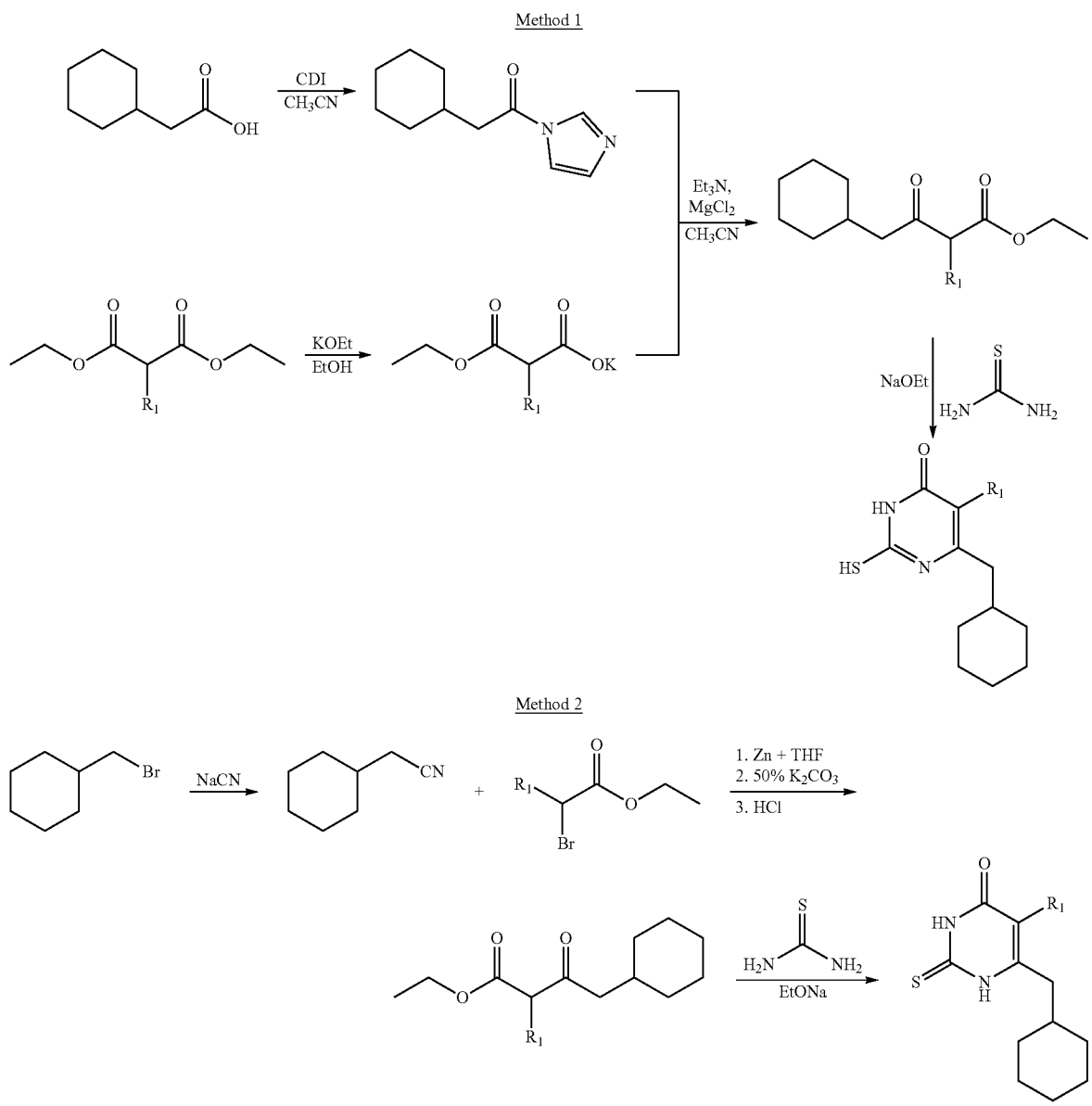

Preparation of Intermediate N-tert-butoxycarbonyl amino acid 2

0.025 mmol of amino acid 1 was added into a 100 mL round bottom flask and dissolved with 50 mL of water and 1,4-dioxane at a volume ratio of 2:1 under stirring, followed by slow addition of 0.05 mmol of NaOH. The resulting mixture was stirred for 0.5 hour and then 0.05 mmol of (Boc)$_2$O was added thereto. The mixture was stirred overnight at room temperature. The reaction was terminated and the solvent was removed by evaporation. The residue was transferred to a beaker with 100 mL of water, the pH of which was adjusted to about 3 with 1N HCl, extracted with 3×50 mL of ethyl acetate. The organic layers were combined, dried over anhydrous Na$_2$SO$_4$, concentrated under reduced pressure to obtain a colorless oily liquid, followed by addition of a mixed solvent of ether and petroleum ether (volume ratio=8:1). The mixture was stirred vigorously to obtain a white solid, filtered by suction and dried to obtain crude N-tert-butoxycarbonyl amino acid 2, which was directly used in the next step without purification.

Preparation of Intermediate 4-(2-bromoacetyl)-N-tert-butoxycarbonyl amino acid ester 4

0.01 mmol of the above N-tert-butoxycarbonyl amino acid 2 was added into a 100 mL round bottom flask and dissolved with dichloromethane, followed by addition of condensing agent DCC (0.012 mmol) and DMAP (0.002 mmol) under stirring. The resulting mixture was stirred in an ice bath for 0.5 hour and then p-hydroxybromoacetophenone (0.011 mmol) was added slowly thereto. After the addition, the mixture was stirred at room temperature, and the reaction was monitored by TLC until the raw materials disappeared completely. The reaction was terminated and filtered by suction. The filtrate was concentrated under reduced pressure, and separated by column chromatography to obtain a pure product of 4-(2-bromoacetyl)-N-tert-butoxycarbonyl amino acid ester 4.

Preparation of 5-alkyl-6-cyclohexylmethyl-2-thio-acetylphenyl-N-tert-butoxycarbonyl amino acid ester 6

3.62 mmol of thiouracil 5 was completely dissolved with 5 mL of DMF in a 50 mL round bottom flask, followed by addition of 4.34 mmol of anhydrous potassium carbonate. The resulting mixture was stirred for 0.5 hour and then a solution of 4-(2-bromoacetyl)-N-tert-butoxycarbonyl amino acid ester 4 (3.98 mmol) in DMF was slowly added thereto. The reaction was performed at a suitable temperature and terminated after TLC detected that the spots of raw materials disappeared. The reaction solution was poured into 50 mL of ice water, stirred vigorously with white turbidity generated, and extracted with 3×50 mL of ethyl acetate. The organic layers were combined and concentrated under reduced pressure to obtain crude 5-alkyl-6-cyclohexylmethyl-2-thio-acetylphenyl-N-tert-butoxycarbonyl amino acid ester 6.

Preparation of 5-alkyl-6-cyclohexyl-2-thioacetylphenyl amino acid ester I 1 mmol of 5-alkyl-6-cyclohexylmethyl-2-thioacetylphenyl-N-tert-butoxycarbonyl amino acid ester 6 was added into a 50 mL round bottom flask and completely dissolved with mL of ethyl acetate under stirring. Saturated amount of HCl gas was introduced and then the resulting mixture was stirred at room temperature for 0.5 hour. The reaction was monitored by TLC and terminated after TLC detected that the spots of raw materials disappeared. The reaction solution was neutralized with saturated sodium carbonate solution until the reaction was no longer vigorous, further neutralized with saturated sodium bicarbonate until no bubble was generated, and a precipitate formed. The mixture was filtered to obtain a crude product of the target product, which was recrystallized to obtain a pure product.

I-1

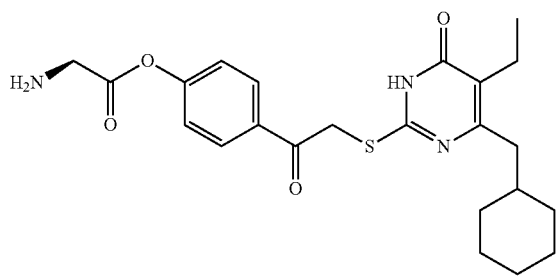

$C_{23}H_{29}N_3O_4S$ (443.56)

According to the above procedure, I-1 was obtained as a white powder with a yield of 56%.

$^1$H NMR (DMSO, 300 MHz) δ 0.68-0.76 (m, 2H, Cyclohexyl-H), 0.83-0.93 (m, 6H, 3H-Cyclohexyl and CH$_2$CH$_3$), 1.26-1.30 (m, 3H, Cyclohexyl-H), 1.43-1.46 (m, 3H, Cyclohexyl-H), 2.15-2.17 (d, 2H, J=6 Hz, CH$_2$-Cyclohexyl), 2.27-2.30 (m, 2H, CH$_2$CH$_3$), 4.09-4.11 (d, 2H, J=6 Hz, NH$_2$—CH$_2$), 4.75 (s, 2H, S—CH$_2$), 7.38-7.40 (d, 2H, J=6 Hz, Ph-H), 8.14-8.17 (d, 2H, J=9 Hz, Ph-H), 8.83 (m, 3H, NH$_2$, NH); $^{13}$C NMR (DMSO, 75 MHz) δ 13.08, 17.85, 25.52 (2C), 25.70, 32.31 (2C), 36.38, 37.57, 39.58, 39.86, 120.61, 121.84 (2C), 130.17 (2C), 134.05, 153.44, 156.94, 159.90, 163.63, 166.08, 191.82.

I-2

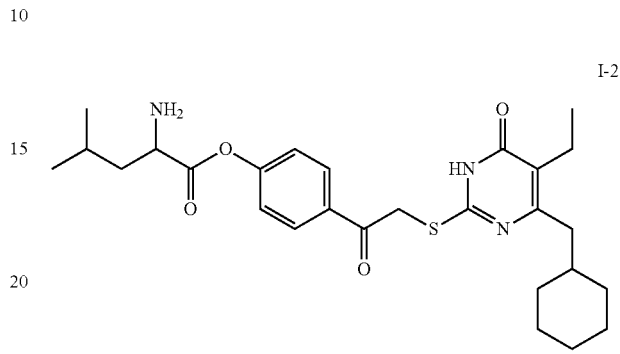

$C_{27}H_{37}N_3O_4S$ (499.25)

According to the above procedure, I-2 was obtained as a pale yellow powder with a yield of 53%.

$^1$H NMR (DMSO, 300 MHz) δ 0.94-0.95 (m, 3H, Cyclohexyl-H), 0.95-0.96 (m, 9H, 3×CH$_3$), 1.24-1.34 (m, 4H, Cyclohexyl-H), 1.42-1.45 (m, 4H, Cyclohexyl-H), 1.61-1.65 (m, 1H, CHMe$_2$), 2.11-2.13 (d, 2H, J=6 Hz, CH$_2$-Cyclohexyl), 2.26-2.29 (m, 2H, CH$_2$CH$_3$), 4.19-4.21 (m, 1H, CH—NH$_2$), 4.72 (s, 2H, S—CH$_2$), 7.41-7.44 (d, 2H, J=9 Hz, Ph-H), 8.15-8.18 (d, 2H, J=9 Hz, Ph-H), 8.52 (brs, H, NH), 9.05 (s, 2H, NH$_2$); $^{13}$C NMR (DMSO, 75 MHz) δ 13.11, 17.86, 21.92, 22.08, 23.88, 25.52 (2C), 25.71, 32.33 (2C), 36.27, 37.05, 37.37, 50.71, 120.74, 121.81 (2C), 130.13, 130.72, 134.21, 153.39, 156.57, 160.07, 163.31, 168.13, 191.98.

I-3

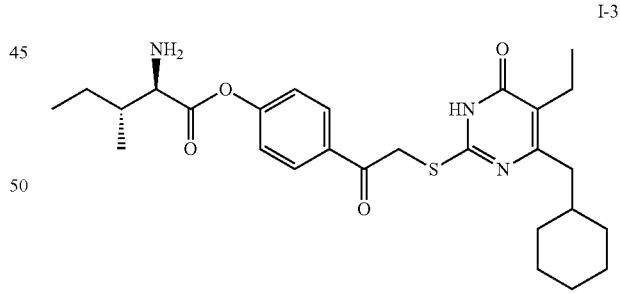

$C_{27}H_{37}N_3O_4S$ (499.25)

According to the above procedure, I-3 was obtained as a light white powder with a yield of 43.27%.

$^1$H NMR (DMSO, 300 MHz) δ 0.66-0.74 (m, 2H, Cyclohexyl-H), 0.87-0.89 (m, 6H, 2CH$_3$), 1.05-1.11 (m, 8H, CHCH$_2$CH$_3$, NH$_2$CHCH$_3$ and 3H-Cyclohexyl), 1.24-1.32 (m, 3H, Cyclohexy-H), 1.41-1.44 (m, 3H, Cyclohexyl-H), 2.11-2.13 (d, 2H, J=6 Hz, CH$_2$-Cyclohexyl), 2.24-2.28 (m, 2H, CH$_2$CH$_3$), 2.36-2.38 (m, 1H, CHCH$_3$), 4.11 (s, 1H, NH$_2$—CH), 4.73 (s, 2H, S—CH$_2$), 7.40-7.43 (d, 2H, J=9 Hz, Ph-H), 8.15-8.17 (d, 2H, J=6 Hz, Ph-H), 9.05 (s, 3H, NH$_2$ and NH);

$^{13}$C NMR (DMSO, 75 MHz) δ 13.06, 17.60, 17.86, 18.62, 25.13, 25.53 (2C), 25.69, 29.43, 32.30 (2C), 36.33, 37.45, 39.84, 57.41, 120.64, 121.84 (2C), 130.17 (2C), 134.20, 153.27, 156.84, 159.93, 163.50, 167.03, 191.90.

120.52, 121.13, 121.70 (2C), 124.97, 129.93 (2C), 106.42, 121.84 (2C), 130.17 (2C), 126.85, 133.96, 136.20, 153.28, 157.16, 159.84, 163.80, 167.70, 191.74.

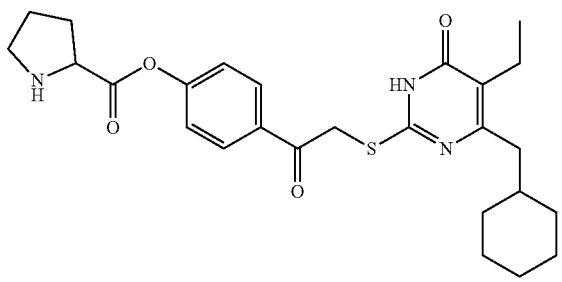

I-4

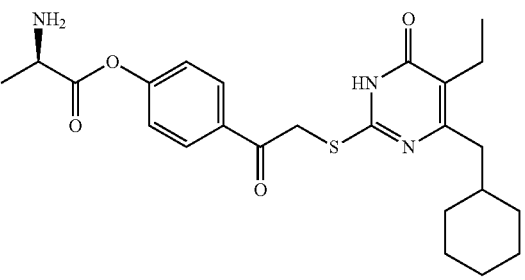

I-6

$C_{26}H_{33}N_3O_4S$ (483.22)

According to the above procedure, I-4 was obtained as a pale yellow powder with a yield of 61%.

$^1$H NMR (DMSO, 300 MHz) δ 0.72-0.79 (m, 2H, Cyclohexyl-H), 0.89-0.93 (m, 6H, CH$_2$C$\underline{H}_3$, 3H-Cyclohexyl), 1.31-1.35 (m, 3H, Cyclohexyl-H), 1.45-1.48 (d, 3H, Cyclohexyl-H), 1.85-1.98 (m, 2H, Pyrrolidinyl-H), 2.17-2.19 (d, 2H, J=6 Hz, C$\underline{H}_2$-Cyclohexyl), 2.24-2.30 (m, 4H, C$\underline{H}_2$CH$_3$ and 2H-Pyrrolidinyl), 3.15-3.21 (m, 2H, Pyrrolidinyl-H), 4.19-4.26 (m, 1H, Pyrrolidinyl-H), 4.65 (s, 2H, C$\underline{H}_2$—S), 6.89-6.92 (d, 2H, J=9 Hz, Ph-H), 7.24 (brs, HCl), 7.89-7.92 (d, 2H, J=9 Hz, Ph-H), 8.80 (s, 1H, NH), 10.28 (brs, 1H, N$\underline{H}$); $^{13}$C NMR (DMSO, 75 MHz) δ 13.04, 17.85, 23.05, 25.49 (2C), 25.72, 27.89, 32.33 (2C), 36.34, 37.19, 39.86, 45.06, 58.52, 115.20 (2C), 120.58, 127.24 130.74 (2C), 157.32, 159.72, 162.53, 163.70, 170.21, 190.85.

$C_{24}H_{31}N_3O_4S$ (457.20)

According to the above procedure, I-6 was obtained as a pale yellow powder with a yield of 47.28%.

$^1$H NMR (DMSO, 300 MHz) δ 0.78-0.92 (m, 10H, CH$_2$C$\underline{H}_3$, NH$_2$CHC$\underline{H}_3$ and 4H-Cyclohexyl), 1.37-1.46 (m, 7H, Cyclohexyl-H), 2.25 (m, 4H, C$\underline{H}_2$CH$_3$ and C$\underline{H}_2$-Cyclohexyl), 3.95-4.00 (m, 1H, NH$_2$—C$\underline{H}$), 4.70 (s, 2H, S—C$\underline{H}_2$), 6.89 (d, 2H, Ph-H), 7.88 (d, 2H, Ph-H), 9.99 (s, 3H, N$\underline{H}$ and N$\underline{H}_2$); $^{13}$C NMR (DMSO, 75 MHz) δ 12.98, 15.78, 17.86, 25.51 (2C), 25.71, 32.29 (2C), 36.49, 37.40, 39.28, 53.07, 115.21 (2C), 120.39, 127.13, 130.76 (2C), 157.93,

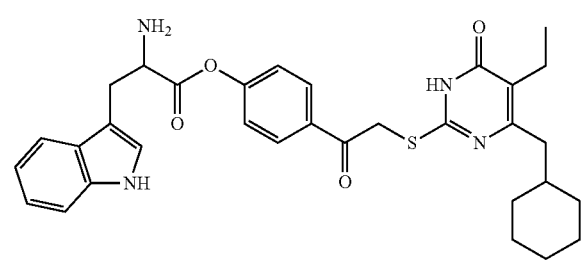

I-5

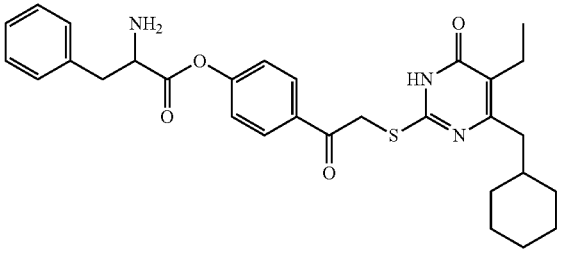

I-7

$C_{32}H_{36}N_4O_4S$ (572.25)

According to the above procedure, I-5 was obtained as a pale yellow powder with a yield of 55.54%.

$^1$H NMR (DMSO, 300 MHz) δ 0.78-0.82 (m, 2H, Cyclohexyl-H), 0.91 (m, 5H, CH$_2$CH$_3$ and 2H-Cyclohexyl), 1.26-1.33 (m, 3H, Cyclohexyl-H), 1.43-1.45 (m, 4H, Cyclohexyl-H), 2.16-2.18 (d, 2H, J=6 Hz, C$\underline{H}_2$-Cyclohexyl), 2.28 (s, 2H, C$\underline{H}_2$CH$_3$), 3.57-3.60 (d, 2H, J=9.9 Hz, C$\underline{H}_2$-indole), 4.45 (m, 1H, C$\underline{H}$—NH$_2$), 4.73 (s, 2H, S—C$\underline{H}_2$), 7.04-7.07 (m, 4H, Ar—H), 7.38-7.39 (d, 2H, J=3 Hz, Ar—H), 7.62-7.65 (d, 1H, J=9 Hz, Ar—H), 8.04-8.07 (d, 2H, J=9 Hz, Ar—H), 9.16 (s, 2H, N$\underline{H}_2$), 11.27 (s, 1H, NH); $^{13}$C NMR (DMSO, 75 MHz) δ 13.04, 17.87, 25.55 (2C), 25.71, 26.23, 32.32 (2C), 36.45, 37.60, 39.61, 53.10, 106.42, 111.61, 118.16, 118.59, $C_{30}H_{35}N_3O_4S$ (533.23)

According to the above procedure, I-7 was obtained as a pale yellow powder with a yield of 42%.

$^1$H NMR (DMSO, 300 MHz) δ 0.77-0.82 (m, 2H, Cyclohexyl-H), 0.90 (m, 6H, 3H-Cyclohexyl and CH$_2$C$\underline{H}_3$), 1.26-1.32 (m, 3H, Cyclohexyl-H), 1.42-1.45 (m, 3H, Cyclohexyl-H), 2.15-2.17 (d, 2H, J=6 Hz, C$\underline{H}_2$-Cyclohexyl), 2.27-2.29 (m, 2H, C$\underline{H}_2$CH$_3$), 3.18-3.25 (m, 2H, C$\underline{H}_2$-Ph) 3.94-4.01 (m, 1H, NH$_2$—C$\underline{H}$), 4.73 (s, 2H, S—C$\underline{H}_2$), 7.13-7.16 (d, 2H, J=9 Hz, Ph-H), 7.27-7.35 (m, 5H, Ph-H), 8.09-8.12 (d, 2H, J=9 Hz, Ph-H), 9.07 (s, 2H, N$\underline{H}_2$), 10.27 (s, H, NH); $^{13}$C NMR (DMSO, 75 MHz) δ 13.01, 17.85, 25.54 (2C), 25.69, 32.30 (2C), 35.98, 36.42, 37.58, 38.68, 53.59, 120.52, 121.61 (2C), 127.30 (2C), 128.56 (2C), 129.49 (2C), 130.06, 134.06, 134.61, 153.13, 159.82, 162.28, 163.79, 167.31, 191.73.

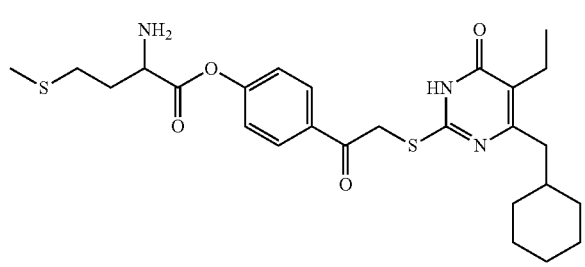

I-8

$C_{26}H_{35}N_3O_4S_2$ (517.21)

According to the above procedure, I-8 was obtained as a pale yellow powder with a yield of 43%.

$^1$H NMR (DMSO, 300 MHz) δ 0.76-0.84 (m, 2H, Cyclohexyl-H), 0.91-1.02 (m, 6H, CH$_2$CH$_3$ and 3H-Cyclohexyl), 1.24-1.32 (m, 3H, Cyclohexyl-H), 1.47-1.54 (m, 3H, Cyclohexyl-H), 2.01 (s, 3H, SCH$_3$), 2.11-2.13 (d, 2H, J=6 Hz, CH$_2$-Cyclohexyl), 2.15-2.17 (m, 2H, CH$_2$CHNH$_2$), 2.25-2.29 (m, 2H, CH$_2$CH$_3$), 2.66-2.70 (t, 2H, J=7.1 Hz, CH$_2$—SCH$_3$), 3.86 (s, 1H, NH$_2$—CH), 4.84 (s, 2H, S—CH$_2$), 7.41-7.44 (d, 2H, J=9 Hz, Ph-H), 8.05-8.10 (d, 2H, J=7 Hz, Ph-H), 9.08 (s, 3H, NH$_2$ and NH); $^{13}$C NMR (DMSO, 75 MHz) δ 13.26, 14.6, 17.87, 25.49 (2C), 25.69 (2C), 29.73, 33.31 (2C), 33.71, 36.13, 36.65, 40.16, 52.13, 119.51, 121.54 (2C), 129.17 (2C), 133.20, 155.75, 157.18, 160.73, 163.40, 168.31, 191.26.

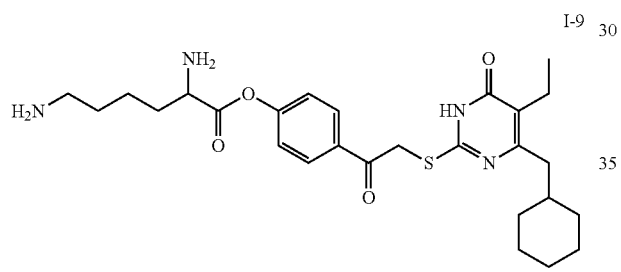

I-9

$C_{27}H_{38}N_4O_4S$ (514.26)

According to the above procedure, I-9 was obtained as a pale yellow powder with a yield of 40.48%.

$^1$H NMR (DMSO, 300 MHz) δ 0.76-0.81 (m, 2H, Cyclohexyl-H), 0.91-0.94 (m, 3H, Cyclohexy-H), 1.22-1.25 (m, 2H, CH$_2$), 1.34-1.48 (m, 6H, Cyclohexy-H), 1.56-1.64 (m, 4H, 2CH$_2$), 1.85-1.87 (m, 2H, CH$_2$), 2.08-2.10 (d, 2H, J=6 Hz, CH$_2$-Cyclohexyl), 2.22-2.24 (m, 2H, CH$_2$CH$_3$), 2.78-2.84 (m, 2H, NH$_2$—CH$_2$), 4.26 (m, 1H, NH$_2$—CH), 4.72 (s, 2H, S—CH$_2$), 7.43-7.45 (d, 2H, J=9 Hz, Ph-H), 8.12-8.14 (d, 2H, J=9 Hz, Ph-H), 8.25 (m, 4H, 2×NH$_2$), 9.04 (s, 1H, NH); $^{13}$C NMR (DMSO, 75 MHz) δ 13.07, 17.86, 25.52 (2C), 25.68, 26.16, 29.16, 32.31 (2C), 36.31, 37.50, 38.14 (2C), 39.28, 51.88, 120.67, 121.96 (2C), 130.07 (2C), 134.13, 153.37, 156.65, 159.95, 163.46, 167.71, 191.90.

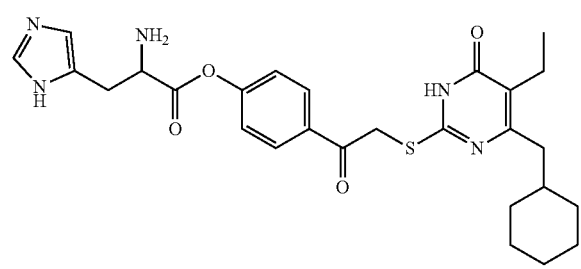

I-10

$C_{27}H_{33}N_5O_4S$ (523.23)

According to the above procedure, I-10 was obtained as a pale yellow powder with a yield of 52%.

$^1$H NMR (DMSO, 300 MHz) δ 0.78-0.82 (m, 2H, Cyclohexyl-H), 0.91-1.02 (m, 6H, CH$_2$CH$_3$ and 3H-Cyclohexyl), 1.24-1.30 (m, 3H, Cyclohexyl-H), 1.42 (m, 3H, Cyclohexyl-H), 2.18-2.26 (m, 2H, CH$_2$-Cyclohexyl), 2.98-3.13 (m, 2H, CH$_2$-imidazol), 4.86 (s, 2H, CH$_2$—S), 6.48-7.51 (d, 3H, J=9 Hz, Ph-H), 7.58 (s, 1H, imidazol-H), 8.02-8.04 (d, 2H, J=6 Hz, Ph-H), 8.47-8.49 (d, 1H, J=6 Hz, imidazol-H), 9.81 (s, 1H, NH), 10.68 (brs, 1H, CONH); $^{13}$C NMR (DMSO, 75 MHz) δ 13.02, 17.85, 25.23 (2C), 26.08, 29.35, 33.17 (2C), 36.07, 37.72, 38.96, 118.60, 120.48, 122.03 (2C), 130.02 (2C), 134.04, 135.91, 154.75, 158.18, 160.78, 163.15, 167.34, 191.91.

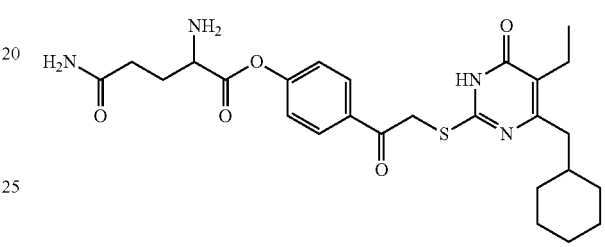

I-11

$C_{26}H_{34}N_4O_5S$ (514.22)

According to the above procedure, I-11 was obtained as a white powder with a yield of 41%.

$^1$H NMR (DMSO, 300 MHz) δ 0.77-0.81 (m, 2H, Cyclohexyl-H), 0.94-0.97 (m, 6H, CH$_2$CH$_3$ and 3H-Cyclohexyl), 1.26-1.36 (m, 3H, Cyclohexyl-H), 1.48-1.51 (m, 3H, Cyclohexyl-H), 1.96-2.01 (m, 2H, CH$_2$CONH$_2$), 2.09-2.11 (d, 2H, J=6 Hz, CH$_2$-Cyclohexyl), 2.12-2.16 (m, 2H, CH$_2$CHNH$_2$), 2.28-2.30 (m, 2H, CH$_2$CH$_3$), 3.66-3.88 (m, 1H, NH$_2$—CH), 4.68 (s, 2H, S—CH$_2$), 6.89-7.01 (d, 2H, J=9 Hz, Ph-H), 7.92-7.95 (d, 2H, J=9 Hz, Ph-H), 10.60 (s, 1H, NH); $^{13}$C NMR (DMSO, 75 MHz) δ 13.18, 17.76, 25.28 (2C), 25.67, 32.26 (2C), 33.22, 36.02, 37.15, 40.68, 52.21, 116.12 (2C), 119.98, 127.68, 130.45 (2C), 155.09, 159.63, 161.08, 162.14, 166.07, 173.62, 192.08.

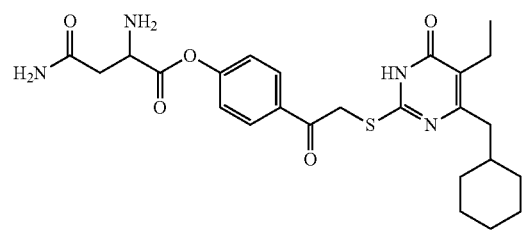

I-12

$C_{25}H_{32}N_4O_5S$ (500.21)

According to the above procedure, I-12 was obtained as a pale yellow powder with a yield of 56.5%.

$^1$H NMR (DMSO, 300 MHz) δ 0.78-0.83 (m, 2H, Cyclohexyl-H), 0.94-0.96 (m, 6H, CH$_2$CH$_3$ and 3H-Cyclohexyl), 1.27-1.33 (m, 3H, Cyclohexyl-H), 1.46-1.50 (m, 3H, Cyclohexyl-H), 2.09-2.11 (d, 2H, J=6 Hz, CH$_2$-Cyclohexyl), 2.17-2.20 (m, 2H, CH$_2$CH$_3$), 2.67-2.92 (m, 2H, CH$_2$CONH$_2$), 3.86-4.01 (m, 1H, NH$_2$—CH), 4.60 (s, 2H, S—CH$_2$), 6.85-6.88 (d, 2H, J=9 Hz, Ph-H), 7.91-7.94 (d, 2H, J=9 Hz, Ph-H), 10.60 (s, 1H, NH); $^{13}$C NMR (DMSO, 75 MHz) δ 13.16, 17.86, 25.49 (2C), 25.97, 32.24 (2C), 36.02, 36.87, 37.15, 40.68, 50.01, 115.12 (2C), 120.98, 127.59, 130.77 (2C), 156.09, 160.63, 161.28, 162.67, 166.07, 172.32, 191.11.

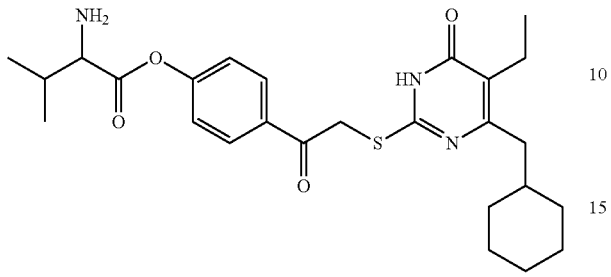

I-13

According to the above procedure, I-13 was obtained as a pale yellow powder with a yield of 58%.

$^1$H NMR (DMSO, 300 MHz) δ 0.89 (s, 6H, CH(C$\underline{H}_3$)$_2$), 1.05-1.11 (m, 8H, CH$_2$C$\underline{H}_3$ and 5H-Cyclohexyl), 1.25-1.28 (d, 3H, J=9 Hz, 3H-Cyclohexyl), 1.42-1.44 (d, 3H, J=6 Hz, Cyclohexyl-H), 2.12 (s, 2H, C$\underline{H}_2$-Cyclohexyl), 2.26-2.36 (m, 2H, C$\underline{H}_2$CH$_3$), 2.37 (m, 1H, C$\underline{H}$Me$_2$), 4.11 (m, 1H, NH$_2$—C$\underline{H}$), 4.73 (s, 2H, S—C$\underline{H}_2$), 7.41-7.43 (d, 2H, J=6 Hz, Ph-H), 8.15-8.17 (d, 2H, J=6 Hz, Ph-H), 9.03 (s, 3H, NH and N$\underline{H}_2$); $^{13}$C NMR (DMSO, 75 MHz) δ 13.07, 17.60, 17.86, 18.62, 25.53 (2C), 25.69, 29.44, 32.31 (2C), 36.32, 37.41, 39.86, 57.41, 120.67, 121.85 (2C), 130.17 (2C), 134.22, 153.27, 156.77, 159.97, 163.46, 167.04, 191.93.

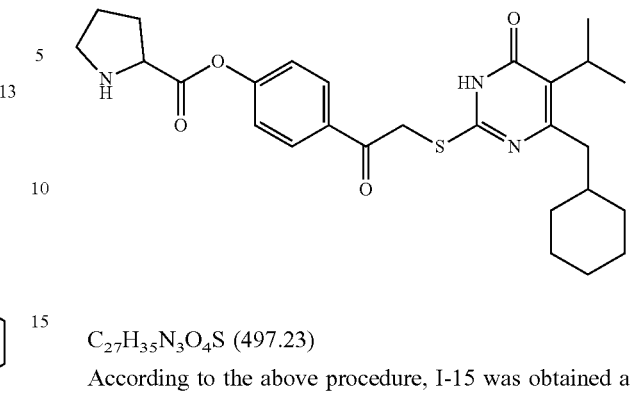

I-15

C$_{27}$H$_{35}$N$_3$O$_4$S (497.23)

According to the above procedure, I-15 was obtained as a pale yellow powder with a yield of 44%.

$^1$H NMR (DMSO, 300 MHz) δ 0.68-0.75 (m, 2H, Cyclohexyl-H), 0.93-0.98 (m, 3H, Cyclohexyl-H), 1.12-1.18 (d, 6H, CH(C$\underline{H}_3$)$_2$), 1.26-1.30 (m, 3H, Cyclohexyl-H), 1.42 (m, 3H, Cyclohexyl-H), 1.98 (m, 3H, Pyrrolidinyl-H), 2.17-2.25 (m, 7H, C$\underline{H}_2$-Cyclohexyl, C$\underline{H}_2$CH$_3$ and 3H-Pyrrolidinyl), 2.89-3.23 (m, 1H, C$\underline{H}$(CH$_3$)$_2$), 4.68 (m, 1H, Pyrrolidinyl-H), 4.76 (s, 2H, C$\underline{H}_2$—S), 6.46-7.49 (d, 2H, J=9 Hz, Ph-H), 8.12-8.14 (d, 2H, J=6 Hz, Ph-H), 9.81 (s, 1H, NH), 10.68 (s, 1H, N$\underline{H}$); $^{13}$C NMR (DMSO, 75 MHz) δ 19.8 (2C), 23.06, 24.4, 25.53 (2C), 25.68, 27.45, 32.28 (2C), 36.47, 37.70, 39.80, 45.26, 58.47, 120.48, 122.03 (2C), 129.28 (2C), 134.04, 153.54, 157.23, 159.78, 163.86, 166.84, 191.82.

I-14

C$_{28}$H$_{39}$N$_3$O$_4$S (513.27)

According to the above procedure, I-14 was obtained as a pale yellow powder with a yield of 47%.

$^1$H NMR (DMSO, 300 MHz) δ 0.76-0.79 (m, 2H, Cyclohexyl-H), 0.87-0.89 (m, 3H, C$\underline{H}_3$), 1.05-1.11 (m, 6H, CH$_3$, and 3H-Cyclohexyl), 1.14-1.21 (d, 6H, CH(C$\underline{H}_3$)$_2$), 1.24-1.32 (m, 3H, Cyclohexyl-H), 1.41-1.44 (m, 3H, Cyclohexyl-H), 2.11-2.13 (d, 2H, J=6 Hz, C$\underline{H}_2$-Cyclohexyl), 2.24-2.28 (m, 2H, C$\underline{H}_2$CH$_3$), 2.36-2.38 (m, 1H, C$\underline{H}$CH$_3$), 2.89-3.29 (m, 1H, C$\underline{H}$(CH$_3$)$_2$), 4.11 (s, 1H, NH$_2$—C$\underline{H}$), 4.76 (s, 2H, S—C$\underline{H}_2$), 7.14-7.23 (d, 2H, Ph-H), 8.12-8.19 (d, 2H, Ph-H), 9.08 (s, 3H, N$\underline{H}_2$ and NH); $^{13}$C NMR (DMSO, 75 MHz) δ 12.16, 15.60, 20.8 (2C), 24.4, 25.3, 25.53 (2C), 25.69, 29.45, 32.32 (2C), 36.36, 37.45, 39.86, 57.42, 120.66, 121.83 (2C), 130.18 (2C), 134.20, 153.25, 156.78, 159.23, 163.52, 167.03, 191.92.

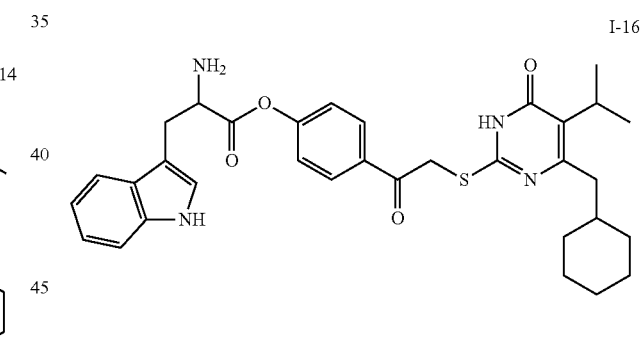

I-16

C$_{33}$H$_{38}$N$_4$O$_4$S (586.26)

According to the above procedure, I-16 was obtained as a pale yellow powder with a yield of 52%.

$^1$H NMR (DMSO, 300 MHz) δ 0.78-0.82 (m, 2H, Cyclohexyl-H), 0.91 (m, 3H, Cyclohexyl-H), 1.22-1.28 (d, 6H, CH(C$\underline{H}_3$)$_2$), 1.31-1.36 (m, 2H, Cyclohexyl-H), 1.43-1.46 (m, 4H, Cyclohexyl-H), 2.26-2.28 (d, 2H, J=6 Hz, C$\underline{H}_2$-Cyclohexyl), 2.97-3.01 (m, 1H, C$\underline{H}$(CH$_3$)$_2$), 3.57-3.60 (d, 2H, J=9.9 Hz, C$\underline{H}_2$-indole), 4.34-4.57 (m, 1H, C$\underline{H}$—NH$_2$), 4.73 (s, 2H, S—C$\underline{H}_2$), 7.06-7.07 (m, 4H, ArH), 7.38-7.39 (d, 2H, J=3 Hz, ArH), 7.62-7.65 (d, 1H, J=9 Hz, ArH), 8.04-8.07 (d, 2H, J=9 Hz, ArH), 9.16 (s, 2H, N$\underline{H}_2$), 11.27 (s, 1H, N$\underline{H}$); $^{13}$C NMR (DMSO, 75 MHz) δ 19.24 (2C), 24.45, 25.55 (2C), 25.71, 27.83, 32.32 (2C), 36.45, 37.58, 39.62, 53.10, 106.42, 111.61, 118.16, 118.59, 120.52, 121.13, 121.70 (2C), 124.97, 129.93 (2C), 106.42, 121.84 (2C), 130.17 (2C), 126.85, 133.96, 136.20, 153.28, 157.16, 159.84, 163.80, 167.70, 191.74.

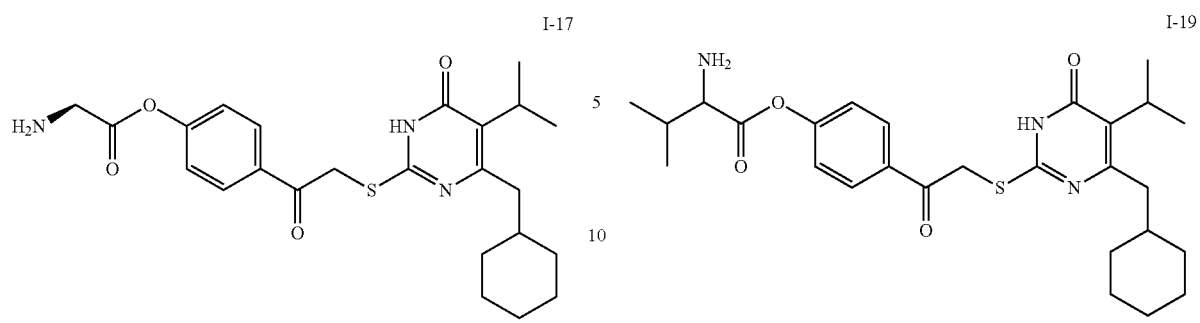

I-17

C$_{24}$H$_{31}$N$_3$O$_4$S (457.20)

According to the above procedure, I-17 was obtained as a pale yellow powder with a yield of 43%.

$^1$H NMR (DMSO, 300 MHz) δ 0.69-0.72 (m, 2H, Cyclohexyl-H), 0.91 (m, 3H, Cyclohexyl-H), 1.20-1.26 (d, 6H, CH(CH$_3$)$_2$), 1.31-1.33 (m, 3H, Cyclohexyl-H), 1.45-1.48 (m, 3H, Cyclohexyl-H), 2.09-2.11 (d, 2H, J=6 Hz, CH$_2$-Cyclohexyl), 2.90-3.13 (m, 1H, CH(CH$_3$)$_2$), 3.71 (s, 2H, NH$_2$—CH$_2$), 4.58 (s, 2H, S—CH$_2$), 6.85-6.88 (d, 2H, J=9 Hz, Ph-H), 7.91-7.94 (d, 2H, J=9 Hz, Ph-H), 8.84 (m, 3H, NH$_2$ and NH); $^{13}$C NMR (DMSO, 75 MHz) δ 19.24 (2C), 24.45, 25.49 (2C), 25.79, 32.44 (2C), 36.00, 37.63, 40.59, 44.27, 115.12 (2C), 120.98, 127.59, 130.77 (2C), 156.09, 160.63, 162.28, 162.67, 166.07, 191.11.

I-19

C$_{27}$H$_{37}$N$_3$O$_4$S (499.25)

According to the above procedure, I-19 was obtained as a pale yellow powder with a yield of 47%.

$^1$H NMR (DMSO, 300 MHz) δ 0.66-0.69 (m, 6H, 2×CH$_3$), 1.05-1.09 (m, 6H, 2×CH$_3$), 1.11-1.28 (m, 8H, Cyclohexyl-H), 1.42-1.44 (d, 3H, J=6 Hz, Cyclohexyl-H), 2.12 (s, 2H, CH$_2$-Cyclohexyl), 2.26 (m, 1H, CHMe$_2$), 2.28 (m, 1H, CHMe$_2$), 4.11 (m, 1H, CH—NH$_2$), 4.73 (s, 2H, S—CH$_2$), 7.40-7.42 (d, 2H, J=6 Hz, Ph-H), 8.13-8.16 (d, 2H, J=6 Hz, Ph-H), 9.08 (s, 3H, NH and NH$_2$); $^{13}$C NMR (DMSO, 75 MHz) δ 19.04 (2C), 17.60, 17.86, 24.44, 25.56 (2C), 25.70, 30.43, 32.31 (2C), 36.32, 37.51, 39.66, 57.48, 121.56, 121.65 (2C), 130.29 (2), 134.12, 153.16, 156.78, 160.02, 163.50, 167.03, 191.91.

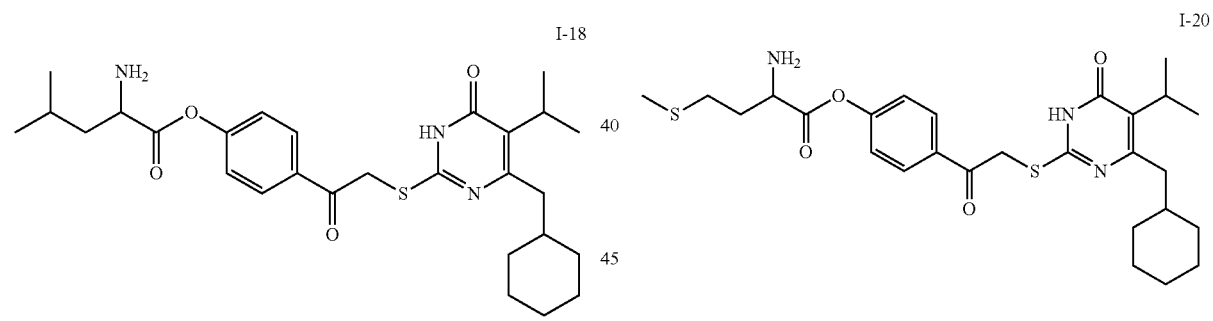

I-18

C$_{28}$H$_{39}$N$_3$O$_4$S (513.27)

According to the above procedure, I-18 was obtained as a pale yellow powder with a yield of 48%.

$^1$H NMR (DMSO, 300 MHz) δ 0.71-0.78 (m, 7H, Cyclohexyl-H), 0.94-0.98 (m, 12H, 4×CH$_3$), 1.32-1.46 (m, 4H, Cyclohexyl-H), 1.60-1.65 (m, 1H, CH(CH$_3$)$_2$), 1.86-1.90 (m, 2H, CH$_2$CH(CH$_3$)$_2$), 2.09-2.12 (d, 2H, CH$_2$-Cyclohexyl), 2.90-3.13 (m, 1H, CH(CH$_3$)$_2$), 3.96-4.02 (m, 1H, CH—NH$_2$), 4.55 (s, 2H, S—CH$_2$), 6.87-6.90 (d, 2H, J=9 Hz, Ph-H), 7.88-7.91 (d, 2H, J=9 Hz, Ph-H); $^{13}$C NMR (DMSO, 75 MHz) δ 19.04 (2C), 23.45, 21.91, 22.00, 25.53 (2C), 25.84, 32.52 (2C), 36.16, 36.57, 40.51, 52.63, 115.26 (2C), 120.56, 127.12, 130.75 (2C), 156.92, 160.32, 162.97, 164.12, 168.14, 191.12.

I-20

C$_{27}$H$_{37}$N$_3$O$_4$S$_2$ (531.22)

According to the above procedure, I-20 was obtained as a pale yellow powder with a yield of 48%.

$^1$H NMR (DMSO, 300 MHz) δ 0.68-0.73 (m, 5H, Cyclohexyl-H), 0.91-1.02 (m, 6H, 2×CH$_3$), 1.21-1.29 (m, 3H, Cyclohexyl-H), 1.41-1.47 (m, 3H, Cyclohexyl-H), 2.07 (s, 3H, SCH$_3$), 2.12-2.14 (d, 2H, J=6 Hz, CH$_2$-Cyclohexyl), 2.14-2.18 (m, 2H, CH$_2$CHNH$_2$), 2.64-2.68 (t, 2H, J=7.1 Hz, CH$_2$—SCH$_3$), 3.89 (s, 1H, NH$_2$—CH), 4.82 (s, 2H, S—CH$_2$), 7.42-7.44 (d, 2H, J=7.5 Hz, Ph-H), 7.96-7.98 (d, 2H, J=7 Hz, Ph-H), 9.07 (s, 3H, NH$_2$ and NH); $^{13}$C NMR (DMSO, 75 MHz) δ 14.97 (SCH$_3$), 19.89 (2C), 24.42, 25.90 (2C), 25.89 (2C), 29.73, 32.31 (2) C, 33.69, 36.13, 36.54, 40.17, 52.12, 119.52, 121.52 (2C), 129.17 (2C), 133.20, 155.75, 157.20, 160.72, 163.44, 168.32, 191.14.

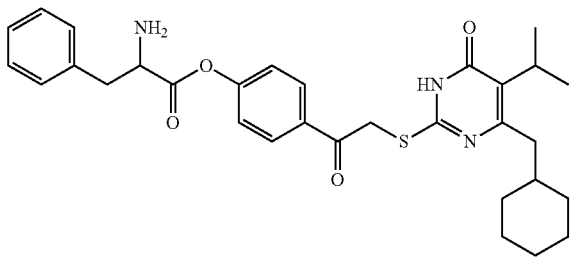

I-21

C₃₁H₃₇N₃O₄S (547.25)

According to the above procedure, I-21 was obtained as a pale yellow powder with a yield of 56%.

¹H NMR (DMSO, 300 MHz) δ 0.87-0.89 (m, 2H, Cyclohexyl-H), 0.90-1.02 (m, 9H, 3H-Cyclohexyl and 2×CH₃), 1.29-1.42 (m, 6H, Cyclohexyl-H), 2.16-2.19 (d, 2H, J=6 Hz, CH₂-Cyclohexyl), 2.78-3.12 (m, 1H, CH(CH₃)₂), 3.19-3.29 (m, 2H, CH₂-Ph) 3.92-4.00 (m, 1H, NH₂—CH), 4.63 (s, 2H, S—CH₂), 7.13-7.16 (d, 2H, J=9 Hz, Ph-H), 7.27-7.35 (m, 5H, Ph-H), 7.92-7.93 (d, 2H, J=9 Hz, Ph-H), 9.08 (s, 2H, NH₂), 10.23 (s, H, NH); ¹³C NMR (DMSO, 75 MHz) δ 20.8 (2C), 23.5, 25.64 (2C), 26.09, 32.31 (2C), 36.99, 36.42, 37.56, 38.63, 53.56, 120.47, 121.58 (2C), 127.31 (2C), 128.48 (2C), 129.51 (2C), 130.11, 134.07, 134.63, 153.71, 159.72, 162.21, 163.43, 167.46, 191.73.

I-23

C₂₂H₂₇N₃O₄S (429.1722)

According to the above procedure, I-23 was obtained as a pale yellow powder with a yield of 58.67%.

¹H NMR (DMSO, 300 MHz) δ 0.75-0.82 (m, 2H, Cyclohexyl-H), 0.95 (s, 3H, Me), 1.33-1.37 (m, 3H, Cyclohexyl-H), 1.46-1.48 (m, 3H, Cyclohexyl-H), 1.82-2.00 (m, 3H, Cyclohexyl-H), 2.23-2.24 (d, 2H, J=6 Hz, CH₂-Cyclohexyl), 3.15-3.19 (t, 2H, J=6 Hz, NH₂—CH₂), 4.68 (s, 2H, S—CH₂), 6.88-6.91 (d, 2H, J=6 Hz, Ph-H), 7.87-7.90 (d, 2H, J=9 Hz, Ph-H), 8.80-8.81 (ds, 2H, NH₂), 10.24-10.25 (ds, 1H, NH); ¹³C NMR (DMSO, 75 MHz) δ 10.29, 23.04, 25.72, 27.89, 32.25, 36.54 37.29, 39.88, 45.07, 114.61, 115.20 (2C), 127.17, 130.75 (2C), 157.57, 160.00, 162.55, 164.52, 170.20, 190.83.

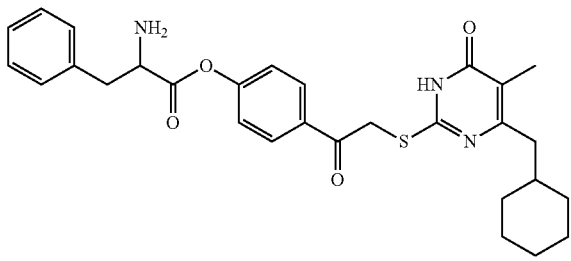

I-22

C₂₉H₃₃N₃O₄S (519.22)

According to the above procedure, I-22 was obtained as a pale yellow powder with a yield of 42%.

¹H NMR (DMSO, 300 MHz) δ 0.77-0.82 (m, 2H, Cyclohexyl-H), 0.96-1.23 (m, 6H, Cyclohexyl-H), 1.52-1.58 (m, 3H, Cyclohexyl-H), 2.12-2.15 (d, 2H, J=6 Hz, CH₂-Cyclohexyl), 2.42 (s, 3H, CH₃), 3.23-3.29 (m, 2H, CH₂-Ph) 3.92-3.98 (m, 1H, CH—NH₂), 4.64 (s, 2H, S—CH₂), 7.13-7.16 (d, 2H, J=9 Hz, Ph-H), 7.27-7.35 (m, 5H, Ph-H), 8.09-8.12 (d, 2H, J=9 Hz, Ph-H), 9.07 (s, 2H, NH₂), 10.27 (s, H, NH); ¹³CNMR (DMSO, 75 MHz) δ 9.55, 25.69 (2C), 26.00, 32.70 (2C), 35.88, 36.32, 37.48, 38.66, 53.57, 120.39, 121.61 (2C), 127.30 (2C), 128.56 (2C), 129.49 (2C), 130.06, 134.06, 134.58, 153.12, 159.76, 162.28, 163.76, 167.30, 191.71.

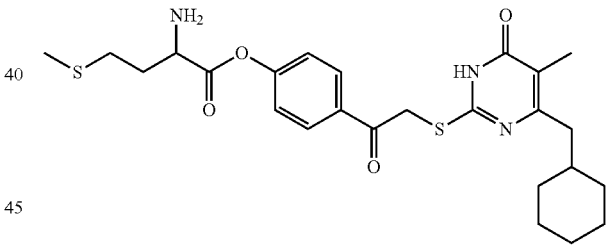

I-24

C₂₅H₃₃N₃O₄S₂ (503.19)

According to the above procedure, I-24 was obtained as a pale yellow powder with a yield of 51%.

¹H NMR (DMSO, 300 MHz) δ 0.76-0.84 (m, 2H, Cyclohexyl-H), 0.91-1.02 (m, 3H, Cyclohexyl-H), 1.26-1.33 (m, 3H, Cyclohexyl-H), 1.46-1.52 (m, 3H, Cyclohexyl-H), 2.02 (s, 1H, SCH₃), 2.11-2.13 (d, 2H, J=6 Hz, CH₂-Cyclohexyl), 2.15-2.17 (m, 2H, CH₂CHNH₂), 2.43 (s, 1H, CH₃), 2.66-2.70 (t, 2H, J=7.1 Hz, CH₂—SCH₃), 3.86 (s, 1H, CH—NH₂), 4.84 (s, 2H, 5-CH₂), 7.41-7.44 (d, 2H, J=9 Hz, Ph-H), 8.05-8.10 (d, 2H, J=7 Hz, Ph-H), 9.08 (s, 3H, NH₂ and NH); ¹³C NMR (DMSO, 75 MHz) δ 9.43, 14.6, 25.49 (2C), 25.69 (2C), 29.73, 33.31 (2C), 33.71, 36.13, 36.65, 40.16, 52.13, 119.51, 121.54 (2C), 129.17 (2C), 133.20, 155.75, 157.18, 160.73, 163.40, 168.31, 191.26.

Effect Example 1: Anti-HIV-1 Activity Test

C8166 cells infected with HIV-1 were used for determining the anti-HIV biological activity at the cellular level. The specific method was described below.

Cytotoxicity experiment: The toxicity of the compounds on C8166 cells was determined by MTT method. In a 96-well cell culture plate, the compounds were subjected to 5-fold serial dilution and 100 μL of C8166 cell suspension ($4\times10^5$/mL) was added into each well. Three replicate wells were set for each concentration. At the same time, a cell control group without drugs and drug control groups with Zidovudine (AZT) or Nevirapine (NVP) were set. The cells were incubated at 37° C. in a 5% $CO_2$ incubator for three days, followed by the addition of MTT solution into each well, and then the cells were incubated at 37° C. for 4 hours. 15% SDS-50% DMF was added to each well and the cells were incubated at 37° C. in a 5% $CO_2$ incubator overnight. After mixing evenly, the OD values were measured by BIO-TEK ELx800 ELISA instrument (determination wavelength: 570 nm; reference wavelength: 630 nm). The dose-response curve was graphed according to the experimental results, and the $CC_{50}$ was calculated (the concentrations of the compounds required to produce toxicity on 50% cells).

Syncytium inhibition experiment: 100 μL of C8166 cell suspension ($4\times10^5$/mL) was inoculated into each well of a 96-well cell culture plate containing 5-fold serial dilutions of the compounds, followed by addition of HIV-$1_{IIIB}$ diluted supernatant (MOI=0.04). Three replicate wells were set for each serial concentration. At the same time, negative control wells of HIV-$1_{IIIB}$ infection without compounds and positive control wells with Zidovudine (AZT) or Nevirapine (NVP) were set. The cells were incubated at 37° C. in a 5% $CO_2$ incubator for three days. The number of the syncytia was counted in five non-overlapping fields of view by using an inverted microscope (100×). The dose-response curves were graphed according to the experimental results, and the 50% effective concentrations of the compounds for inhibiting the virus (EC50, 50% effective concentration) were calculated according to Reed & Muench method. Calculation formula: cytopathic inhibition rate (%)=(1−number of syncytia in experimental wells/number of syncytia in control well)× 100%.

In the present disclosure, AZT and NVP were used as control, and the inhibitory activity data of some target compounds on HIV-$1_{IIIB}$ is shown in Table 1:

TABLE 1

Inhibitory activity data of target compounds on HIV-$1_{IIIB}$

| No. | $CC_{50}$ (μM) | $EC_{50}$ (μM) | SI |
|---|---|---|---|
| I-1 | 137.6 | 0.004 | 33686 |
| I-2 | 112.0 | 0.003 | 48217 |
| I-3 | 134.3 | 0.005 | 31375 |
| I-4 | 95.38 | 0.012 | 9233 |
| I-5 | 95.19 | 0.004 | 23911 |
| I-6 | 96.01 | 0.004 | 25390 |
| I-7 | 90.14 | 0.009 | 11002 |
| I-8 | 116.0 | 0.004 | 30582 |
| I-9 | 100.7 | 0.006 | 19235 |
| I-10 | 199.3 | 0.012 | 15445 |
| I-11 | 117.6 | 0.005 | 23787 |
| I-12 | 120.3 | 0.004 | 30183 |
| I-13 | 94.75 | 0.003 | 54286 |
| I-14 | 186.2 | 0.004 | 42237 |
| I-15 | 98.26 | 0.012 | 7963.9 |
| I-16 | 118.4 | 0.004 | 31257 |
| I-17 | 190.6 | 0.003 | 63936 |

TABLE 1-continued

Inhibitory activity data of target compounds on HIV-$1_{IIIB}$

| No. | $CC_{50}$ (μM) | $EC_{50}$ (μM) | SI |
|---|---|---|---|
| I-18 | 97.39 | 0.004 | 40305 |
| I-19 | 125.60 | 0.003 | 37677 |
| I-20 | 153.1 | 0.003 | 44946 |
| I-21 | 94.98 | 0.004 | 31050 |
| I-22 | 98.58 | 0.010 | 9217.3 |
| I-23 | >200 | 0.008 | >12656 |
| I-24 | 199.3 | 0.012 | 19616 |
| AZT | >749 | 0.049 | >15286 |
| NVP | 504.1 | 0.013 | 38777 |

It can be seen from Table 1 that the amino acid ester derivatives of DACOs of the present disclosure are a series of novel type of non-nucleoside HIV-1 inhibitors and have high inhibitory activities on HIV-1 virus strains. As shown in Table 1, the $EC_{50}$ values of the twenty four preferred compounds for inhibiting HIV-1 virus strains all reach nanomolar levels, and the cytotoxicities of which are relatively low ($CC_{50}$ values range between 85 μM and 199 μM). The compounds other than compounds I-4, I-15 and I-22 have selectivity indexes (SI) greater than 10000 which are equivalent to AZT, and compounds I-2, I-13, I-14, I-17, I-18 and I-20 have selectivity indexes higher than AZT and NVP, and thus these compounds can be used as anti-HIV drug candidates.

Although the specific embodiments of the present disclosure have been described above, those skilled in the art should understand that these embodiments are only intended for illustration, and various changes or variations can be made to these embodiments without departing from the spirit and essence of the present disclosure. Therefore, the scope of protection of the present disclosure is defined by the appended claims.

What is claimed is:

1. A DACOs-type NNRTIs amino acid ester derivative represented by formula I, or a tautomer, optical isomer, hydrate, solvate, polymorph or pharmaceutically acceptable salt thereof:

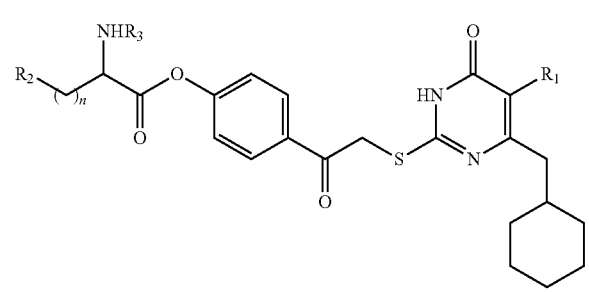

wherein:
$R_1$ is H, $C_1$-$C_6$ branched or straight chain alkyl, or $C_3$-$C_6$ cycloalkyl;
n is an integer between 0 and 8;
$R_2$ is H, $C_1$-$C_{12}$ straight or branched chain alkyl, $C_3$-$C_6$ cycloalkyl, —$C_1$-$C_{12}$ straight or branched chain alkyl-$NH_2$, —$C_1$-$C_{12}$ straight or branched chain alkyl-OH, $NH_2C(=O)$—, $C_1$-$C_{12}$ straight or branched chain alkoxy, $C_1$-$C_{12}$ straight or branched chain alkylthio, $C_6$-$C_{20}$ aryl, $C_2$-$C_{10}$ heteroaryl, $C_6$-$C_{20}$ aryl substituted by one or more $R_{2a}$, or $C_2$-$C_{10}$ heteroaryl substituted by one or more $R_{2b}$; wherein each of $R_{2a}$ and $R_{2b}$ is independently selected from hydroxyl, nitro, halogen, amino, cyano, sulfo group, $C_1$-$C_6$ branched or straight chain alkyl, $C_1$-$C_6$ branched or straight chain alkoxy, $C_1$-$C_6$ branched or straight chain alkylthio, $C_1$-$C_6$ branched or straight chain haloalkyl, and when the number of $R_{2a}$ or $R_{2b}$ is more, then each $R_{2a}$ or each $R_{2b}$ is the same or different;

$R_3$ is H, or $R_2$ and $R_3$ together with the structural fragment to which they are attached form $C_2$-$C_6$ heterocycloalkyl.

2. The DACOs-type NNRTIs amino acid ester derivative represented by formula I as defined in claim 1, wherein, when $R_1$ is $C_1$-$C_6$ branched or straight chain alkyl, then the $C_1$-$C_6$ branched or straight chain alkyl is $C_1$-$C_3$ branched or straight chain alkyl;

when $R_1$ is $C_3$-$C_6$ cycloalkyl, then the $C_3$-$C_6$ cycloalkyl is cyclopropyl, cyclobutyl, cyclopentyl or cyclohexyl;

when $R_2$ is $C_1$-$C_{12}$ branched or straight chain alkyl, then the $C_1$-$C_{12}$ branched or straight chain alkyl is $C_1$-$C_6$ branched or straight chain alkyl;

when $R_2$ is $C_3$-$C_6$ cycloalkyl, then the $C_3$-$C_6$ cycloalkyl is cyclopropyl, cyclobutyl, cyclopentyl or cyclohexyl;

when $R_2$ is —$C_1$-$C_{12}$ straight or branched chain alkyl-$NH_2$, then the $C_1$-$C_{12}$ straight or branched chain alkyl is $C_1$-$C_6$ branched or straight chain alkyl;

when $R_2$ is —$C_1$-$C_{12}$ straight or branched chain alkyl-OH, then the $C_1$-$C_{12}$ straight or branched chain alkyl is $C_1$-$C_6$ branched or straight chain alkyl;

when $R_2$ is $C_1$-$C_{12}$ straight or branched chain alkoxy, then the $C_1$-$C_{12}$ straight or branched chain alkoxy is $C_1$-$C_6$ branched or straight chain alkoxy;

when $R_2$ is $C_1$-$C_{12}$ straight or branched chain alkylthio, then the $C_1$-$C_{12}$ straight or branched chain alkylthio is $C_1$-$C_6$ branched or straight chain alkylthio;

when $R_2$ is $C_6$-$C_{20}$ aryl, then the $C_6$-$C_{20}$ aryl is $C_6$-$C_{10}$ aryl;

when $R_2$ is $C_2$-$C_{10}$ heteroaryl, then the $C_2$-$C_{10}$ heteroaryl is $C_2$-$C_8$ heteroaryl;

when $R_2$ is $C_6$-$C_{20}$ aryl substituted by one or more $R_{2a}$, then the $C_6$-$C_{20}$ aryl is $C_6$-$C_{10}$ aryl;

when $R_2$ is $C_2$-$C_{10}$ heteroaryl substituted by one or more $R_{2b}$, then the $C_2$-$C_{10}$ heteroaryl is $C_2$-$C_8$ heteroaryl;

when $R_2$ and $R_3$ together with the structural fragment to which they are attached form $C_2$-$C_6$ heterocycloalkyl, then the $C_2$-$C_6$ heterocycloalkyl is azacyclohexyl, azacyclopentyl or azacyclobutyl;

when $R_{2a}$ or $R_{2b}$ is halogen, then the halogen is fluorine, chlorine, bromine or iodine;

when $R_{2a}$ or $R_{2b}$ is $C_1$-$C_6$ branched or straight chain alkyl, then the $C_1$-$C_6$ branched or straight chain alkyl is $C_1$-$C_3$ branched or straight chain alkyl;

when $R_{2a}$ or $R_{2b}$ is $C_1$-$C_6$ branched or straight chain alkoxy, then the $C_1$-$C_6$ branched or straight chain alkoxy is $C_1$-$C_3$ branched or straight chain alkoxy;

when $R_{2a}$ or $R_{2b}$ is $C_1$-$C_6$ branched or straight chain alkylthio, then the $C_1$-$C_6$ branched or straight chain alkylthio is $C_1$-$C_3$ branched or straight chain alkylthio;

when $R_{2a}$ or $R_{2b}$ is $C_1$-$C_6$ branched or straight chain haloalkyl, then the $C_1$-$C_6$ branched or straight chain haloalkyl is $C_1$-$C_3$ straight or branched chain haloalkyl;

when $R_2$ is $C_2$-$C_{10}$ heteroaryl substituted by one or more $R_{2b}$, then the position through which the $C_2$-$C_{10}$ heteroaryl is connected to the rest of the DACOs-type NNRTIs amino acid ester derivative represented by formula I is 2-position, 3-position or 4-position of the heteroaryl;

and/or, n is 0, 1, 2, 3, 4, 5, 6, 7 or 8.

3. The DACOs-type NNRTIs amino acid ester derivative represented by formula I as defined in claim 1, wherein, when $R_1$ is $C_1$-$C_6$ branched or straight chain alkyl, then the $C_1$-$C_6$ branched or straight chain alkyl is isopropyl, n-propyl, ethyl or methyl;

when $R_2$ is $C_1$-$C_{12}$ branched or straight chain alkyl, then the $C_1$-$C_{12}$ branched or straight chain alkyl is $C_1$-$C_4$ branched or straight chain alkyl;

when $R_2$ is —$C_1$-$C_{12}$ straight or branched chain alkyl-$NH_2$, then the $C_1$-$C_{12}$ straight or branched chain alkyl is $C_1$-$C_4$ branched or straight chain alkyl;

when $R_2$ is —$C_1$-$C_{12}$ straight or branched chain alkyl-OH, then the $C_1$-$C_{12}$ straight or branched chain alkyl is $C_1$-$C_4$ branched or straight chain alkyl;

when $R_2$ is $C_1$-$C_{12}$ straight or branched chain alkoxy, then the $C_1$-$C_{12}$ straight or branched chain alkoxy is $C_1$-$C_3$ branched or straight chain alkoxy;

when $R_2$ is $C_1$-$C_{12}$ straight or branched chain alkylthio, then the $C_1$-$C_{12}$ straight or branched chain alkylthio is $C_1$-$C_3$ branched or straight chain alkylthio;

when $R_2$ is $C_6$-$C_{20}$ aryl, then the $C_6$-$C_{20}$ aryl is phenyl;

when $R_2$ is $C_2$-$C_{10}$ heteroaryl, then the $C_2$-$C_{10}$ heteroaryl is pyridyl, pyridazinyl, pyrimidinyl, pyrazinyl, furanyl, thienyl, pyrrolyl, pyrazolyl, indolyl, isoindolyl, imidazolyl, oxazolyl, isoxazolyl, thiazolyl, pyrimidinonyl, oxadiazolyl, pyridonyl or triazolyl;

when $R_2$ is $C_6$-$C_{20}$ aryl substituted by one or more $R_{2a}$, then the $C_6$-$C_{20}$ aryl is phenyl;

when $R_2$ is $C_2$-$C_{10}$ heteroaryl substituted by one or more $R_{2b}$, then the $C_2$-$C_{10}$ heteroaryl is pyridyl, pyridazinyl, pyrimidinyl, pyrazinyl, furanyl, thienyl, pyrrolyl, pyrazolyl, indolyl, isoindolyl, imidazolyl, oxazolyl, isoxazolyl, thiazolyl, pyrimidinonyl, oxadiazolyl, pyridonyl or triazolyl;

when $R_{2a}$ or $R_{2b}$ is $C_1$-$C_6$ branched or straight chain alkyl, then the $C_1$-$C_6$ branched or straight chain alkyl is methyl, ethyl, n-propyl or isopropyl when $R_{2a}$ or $R_{2b}$ is $C_1$-$C_6$ branched or straight chain alkoxy, then the $C_1$-$C_6$ branched or straight chain alkoxy is methoxy, ethoxy, propoxy or isopropoxy;

when $R_{2a}$ or $R_{2b}$ is $C_1$-$C_6$ branched or straight chain alkylthio, then the $C_1$-$C_6$ branched or straight chain alkylthio is methylthio, ethylthio, propylthio or isopropylthio;

when $R_{2a}$ or $R_{2b}$ is $C_1$-$C_6$ branched or straight chain haloalkyl, then the $C_1$-$C_6$ branched or straight chain haloalkyl is trifluoromethyl, difluoromethyl, or 1,2-difluoroethyl.

4. The DACOs-type NNRTIs amino acid ester derivative represented by formula I as defined in claim 1, wherein, when $R_2$ is $C_1$-$C_{12}$ branched or straight chain alkyl, then the $C_1$-$C_{12}$ branched or straight chain alkyl is methyl, ethyl, propyl, isopropyl, n-butyl, isobutyl, sec-butyl or tert-butyl;

when $R_2$ is —$C_1$-$C_{12}$ straight or branched chain alkyl-$NH_2$, then the $C_1$-$C_{12}$ straight or branched chain alkyl is methyl, ethyl, propyl, isopropyl, n-butyl, isobutyl, sec-butyl or tert-butyl;

when $R_2$ is —$C_1$-$C_{12}$ straight or branched chain alkyl-OH, then the $C_1$-$C_{12}$ straight or branched chain alkyl is methyl, ethyl, propyl, isopropyl, n-butyl, isobutyl, sec-butyl or tert-butyl;

when $R_2$ is $C_1$-$C_{12}$ straight or branched chain alkoxy, then the $C_1$-$C_{12}$ straight or branched chain alkoxy is methoxy, ethoxy, n-propoxy or isopropoxy;

when $R_2$ is $C_1$-$C_{12}$ straight or branched chain alkylthio, then the $C_1$-$C_{12}$ straight or branched chain alkylthio is methylthio, ethylthio, n-propylthio or isopropylthio.

5. The DACOs-type NNRTIs amino acid ester derivative represented by formula I as defined in claim 1, wherein, $R_1$ is methyl, ethyl or isopropyl;

and/or, n is 0, 1 or 2;

and/or, $R_3$ is H;

and/or, $R_2$ is H, $C_1$-$C_{12}$ straight or branched chain alkyl, —$C_1$-$C_{12}$ straight or branched chain alkyl-$NH_2$, $NH_2C(=O)$—, $C_1$-$C_{12}$ straight or branched chain alkoxy, $C_1$-$C_{12}$ straight or branched chain alkylthio, $C_6$-$C_{20}$ aryl, $C_2$-$C_{10}$ heteroaryl, $C_6$-$C_{20}$ aryl substituted by one or more $R_{2a}$ or $C_2$-$C_{10}$ heteroaryl substituted by one or more $R_{2b}$; said one or more is 1-6.

6. The DACOs-type NNRTIs amino acid ester derivative represented by formula I as defined in claim 1, wherein, when $R_2$ is $C_6$-$C_{20}$ aryl substituted by one or more $R_{2a}$ or $C_2$-$C_{10}$ heteroaryl substituted by one or more $R_{2b}$, then said one or more is 1-3.

7. The DACOs-type NNRTIs amino acid ester derivative represented by formula I as defined in claim 1, wherein, when $R_2$ is $C_6$-$C_{20}$ aryl substituted by one or more Rea or $C_2$-$C_{10}$ heteroaryl substituted by one or more $R_{2b}$, then said one or more is 1-2.

8. The DACOs-type NNRTIs amino acid ester derivative represented by formula I as defined in claim 1, wherein, $R_1$ is ethyl or isopropyl, n is 0, 1 or 2, $R_3$ is H, $R_2$ is H, $C_1$-$C_{12}$ straight or branched chain alkyl, —$C_1$-$C_{12}$ straight or branched chain alkyl-$NH_2$, $NH_2C(=O)$—, $C_1$-$C_{12}$ straight or branched chain alkoxy, $C_1$-$C_{12}$ straight or branched chain alkylthio, $C_6$-$C_{20}$ aryl or $C_2$-$C_{10}$ heteroaryl;

or, $R_1$ is ethyl or isopropyl, n is 0, 1 or 2, $R_3$ is H, $R_2$ is H, isopropyl, isobutyl, sec-butyl or methylthio.

9. The DACOs-type NNRTIs amino acid ester derivative represented by formula I as defined in claim 1, wherein, the structural unit

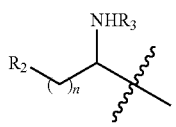

contained in the DACOs-type NNRTIs amino acid ester derivative represented by formula I is

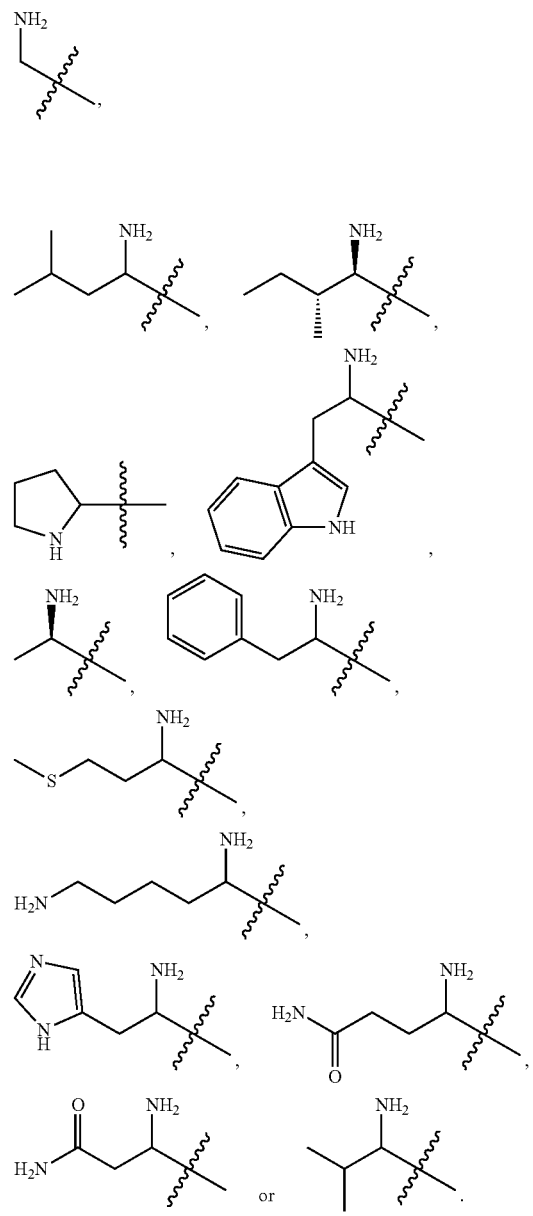

10. The DACOs-type NNRTIs amino acid ester derivative represented by formula I as defined in claim 1, wherein, the DACOs-type NNRTIs amino acid ester derivative represented by formula I is any of the following compounds:

| No. | Structure |
| --- | --- |
| I-1 | 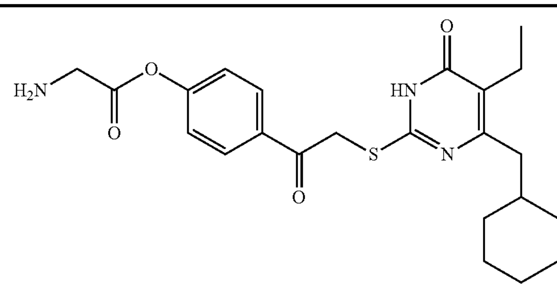 |

-continued

| No. | Structure |
|---|---|
| I-2 | 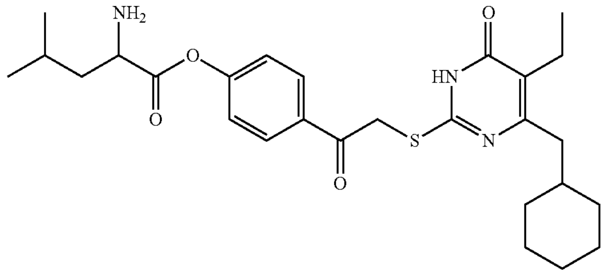 |
| I-3 | 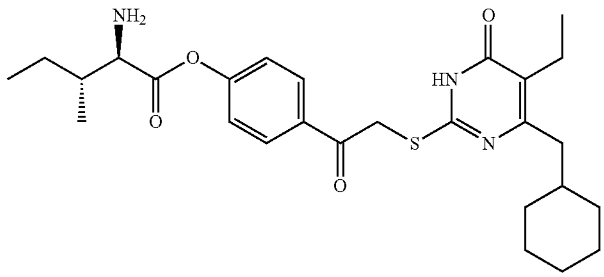 |
| I-4 | 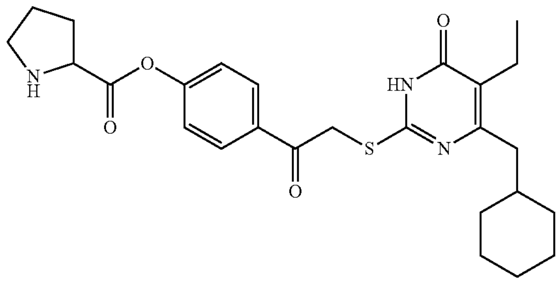 |
| I-5 | 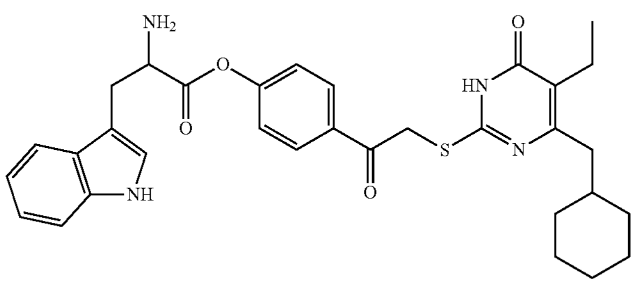 |
| I-6 | 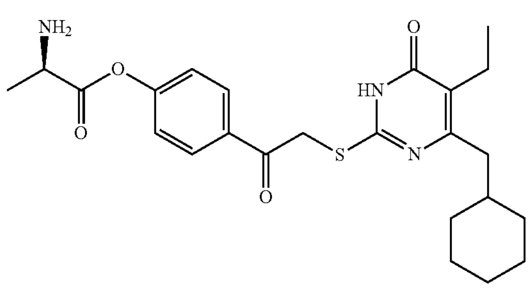 |

| No. | Structure |
|---|---|
| I-7 | 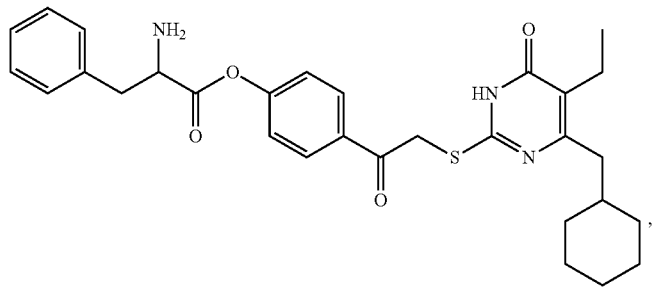 [SMILES: CCc1c(CC2CCCCC2)nc(SCC(=O)c2ccc(OC(=O)C(N)Cc3ccccc3)cc2)[nH]c1=O] |
| I-8 | 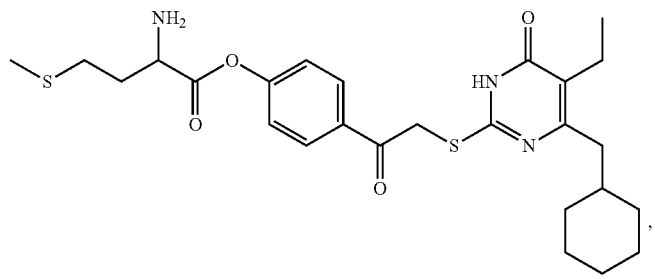 |
| I-9 | 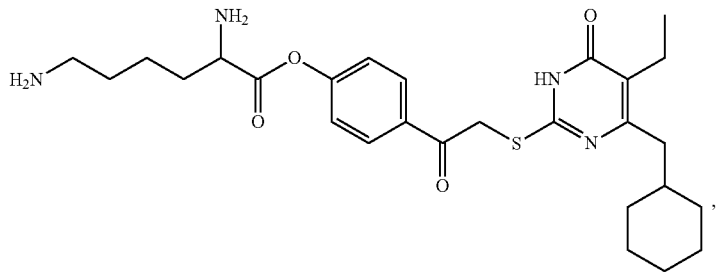 [SMILES: CCc1c(CC2CCCCC2)nc(SCC(=O)c2ccc(OC(=O)C(N)CCCCN)cc2)[nH]c1=O] |
| I-10 | 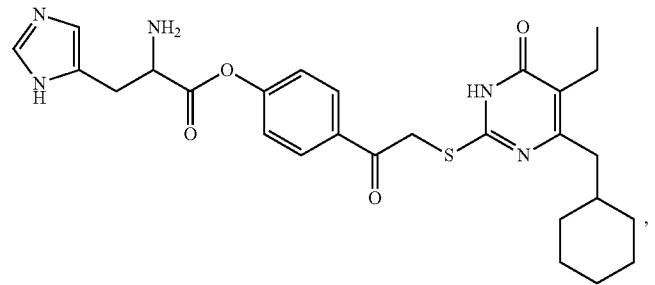 [SMILES: CCc1c(CC2CCCCC2)nc(SCC(=O)c2ccc(OC(=O)C(N)Cc3cnc[nH]3)cc2)[nH]c1=O] |
| I-11 | 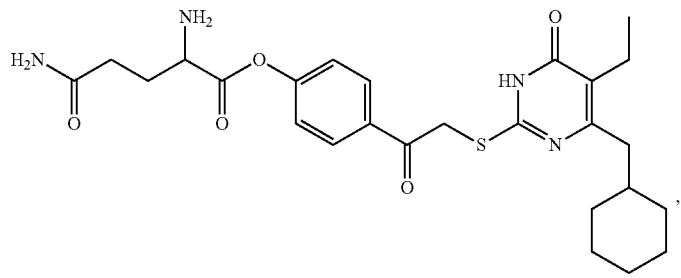 [SMILES: CCc1c(CC2CCCCC2)nc(SCC(=O)c2ccc(OC(=O)C(N)CCC(N)=O)cc2)[nH]c1=O] |

| No. | Structure |
|---|---|
| I-12 | (structure of compound I-12: asparagine ester of 4-hydroxyphenacyl-thio-pyrimidinone with 5-ethyl and 6-cyclohexylmethyl substituents) |
| I-13 | (structure of compound I-13: valine ester of 4-hydroxyphenacyl-thio-pyrimidinone with 5-ethyl and 6-cyclohexylmethyl substituents) |
| I-14 | (structure of compound I-14: isoleucine ester of 4-hydroxyphenacyl-thio-pyrimidinone with 5-isopropyl and 6-cyclohexylmethyl substituents) |
| I-15 | (structure of compound I-15: proline ester of 4-hydroxyphenacyl-thio-pyrimidinone with 5-isopropyl and 6-cyclohexylmethyl substituents) |
| I-16 | (structure of compound I-16: tryptophan ester of 4-hydroxyphenacyl-thio-pyrimidinone with 5-isopropyl and 6-cyclohexylmethyl substituents) |

-continued
| No. | Structure |
|---|---|
| I-17 | 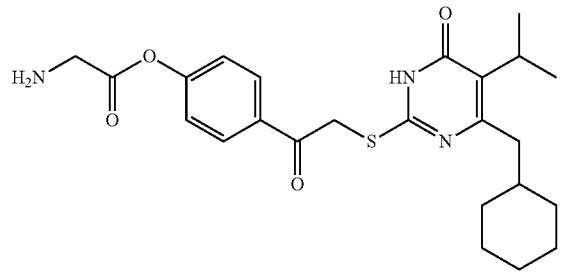 |
| I-18 | 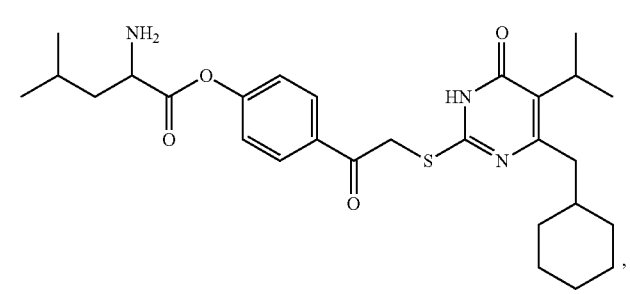 [SMILES: CC(C)CC(N)C(=O)Oc1ccc(C(=O)CSc2nc(CC3CCCCC3)c(C(C)C)c(=O)[nH]2)cc1] |
| I-19 | 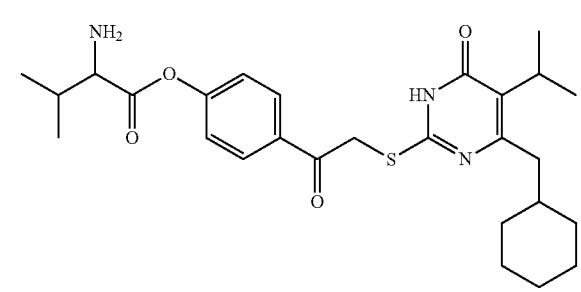 |
| I-20 | 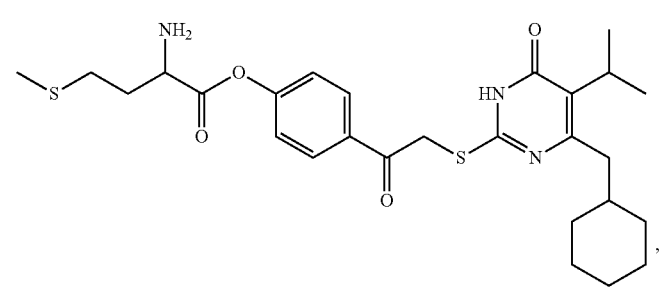 [SMILES: CSCCC(N)C(=O)Oc1ccc(C(=O)CSc2nc(CC3CCCCC3)c(C(C)C)c(=O)[nH]2)cc1] |
| I-21 | 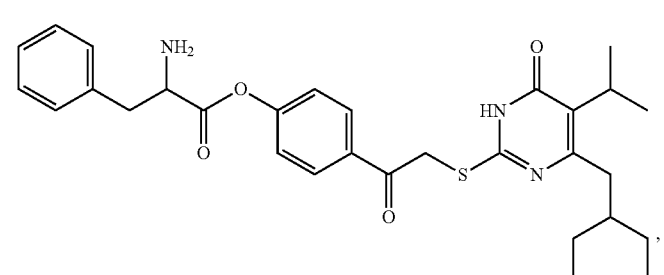 |

| No. | Structure |
|---|---|
| I-22 | 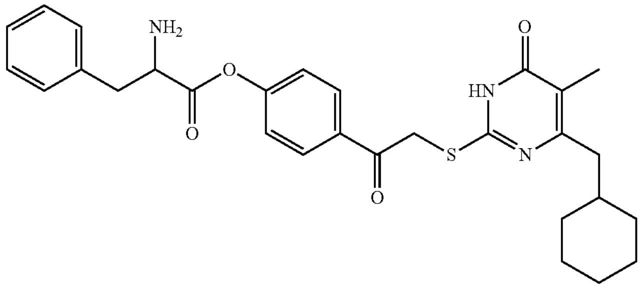 |
| I-23 | 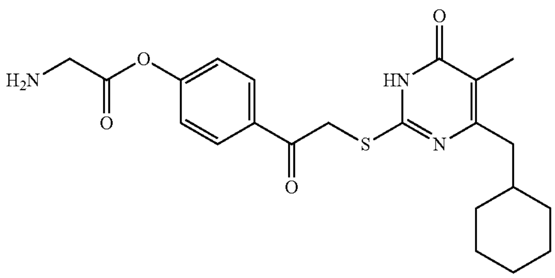 |
| I-24 | 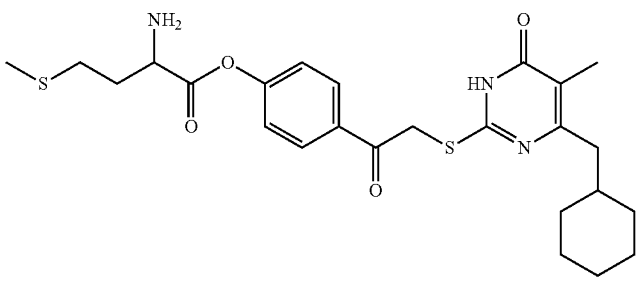 |

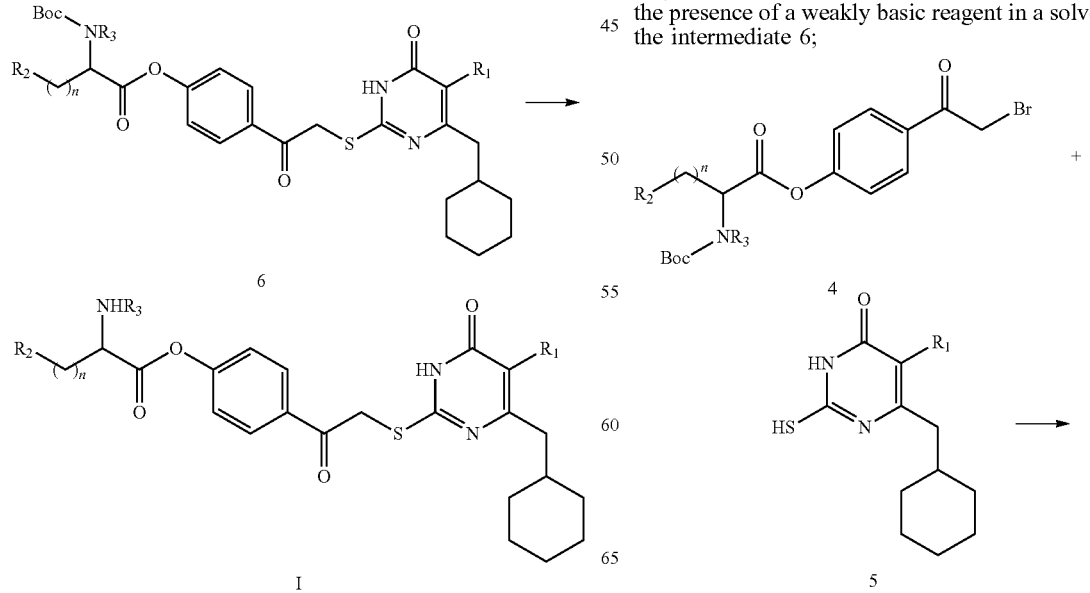

11. A method for preparing the DACOs-type NNRTIs amino acid ester derivative represented by formula I as defined in claim 1, comprising carrying out a Boc removal reaction of intermediate 6 in the presence of an acidic reagent in a solvent;

wherein the definitions of n, $R_1$, $R_2$ and $R_3$ are as defined in claim 1.

12. The method as defined in claim 11 for preparing the DACOs-type NNRTIs amino acid ester derivative represented by formula I, further comprising carrying out an alkylation reaction of intermediate 4 and intermediate 5 in the presence of a weakly basic reagent in a solvent to obtain the intermediate 6;

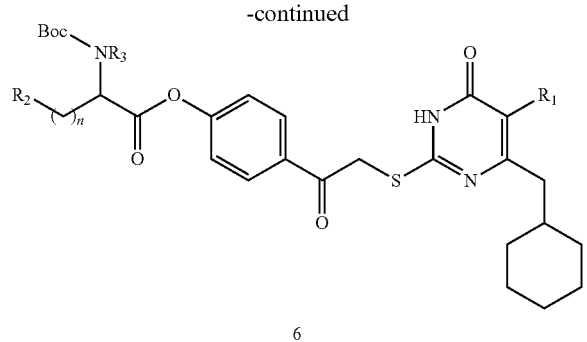

6 wherein the definitions of n, $R_1$, $R_2$ and $R_3$ are as defined in claim 11.

13. The method as defined in claim 12 for preparing the DACOs-type NNRTIs amino acid ester derivative represented by formula I, further comprising carrying out a condensation reaction of intermediate 2 and intermediate 3 in the presence of a catalyst and a condensing agent in a solvent to obtain the intermediate 4;

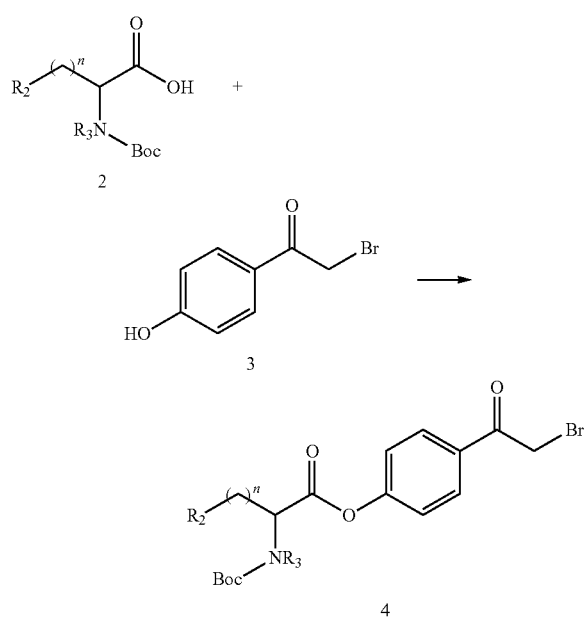

wherein the definitions of n, $R_2$ and $R_3$ are as defined in claim 12.

14. The method as defined in claim 13 for preparing the DACOs-type NNRTIs amino acid ester derivative represented by formula I, further comprising carrying out a N-Boc protection reaction of intermediate 1 with $(Boc)_2O$ in the presence of a base in a solvent to obtain the intermediate 2;

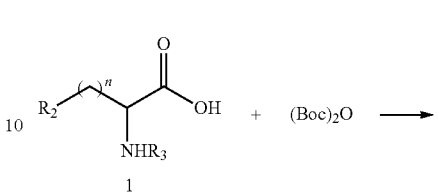

1

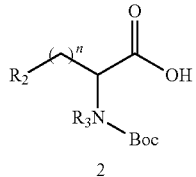

2 wherein the definitions of n, $R_2$ and $R_3$ are as defined in claim 13.

15. A method for inhibiting non-nucleoside HIV-1 in a subject in need thereof, comprising administering a therapeutically effective amount of the DACOs-type NNRTIs amino acid ester derivative represented by formula I, the tautomer, optical isomer, hydrate, solvate, polymorph or pharmaceutically acceptable salt thereof as defined in claim 1 to the subject in need thereof.

16. The method as defined in claim 15, wherein the non-nucleoside HIV-1 is non-nucleoside HIV-1$_{IIIB}$.

17. A method for treating human immunodeficiency virus infection in a subject in need thereof, comprising administering the DACOs-type NNRTIs amino acid ester derivative represented by formula I, the tautomer, optical isomer, hydrate, solvate, polymorph or pharmaceutically acceptable salt thereof as defined in claim 1 to the subject.

18. A pharmaceutical composition comprising a therapeutically effective amount of the DACOs-type NNRTIs amino acid ester derivative represented by formula I, the tautomer, optical isomer, hydrate, solvate, polymorph or pharmaceutically acceptable salt thereof as defined in claim 1, and at least one pharmaceutical excipient.

19. A method for treating human immunodeficiency virus infection disease in a subject in need thereof, wherein the method comprises administering a therapeutically effective amount of the pharmaceutical composition as defined in claim 18 to the subject.

* * * * *